(12) United States Patent
Sattler et al.

(10) Patent No.: US 11,713,364 B2
(45) Date of Patent: Aug. 1, 2023

(54) PROCESSES FOR POLYMERIZING ALPHA-OLEFINS, INTERNAL OLEFINS AND COMPOSITIONS THEREOF

(71) Applicant: ExxonMobil Technology and Engineering Company, Annandale, NJ (US)

(72) Inventors: Aaron Sattler, Annandale, NJ (US); Suzzy C. H. Ho, Princeton, NJ (US); Michele L. Paccagnini, Randolph, NJ (US); Christian E. Padilla, Mountain View, CA (US)

(73) Assignee: Exxon Mobil Technology and Engineering Company, Annandale, NJ (US)

( * ) Notice: Subject to any disclaimer, the term of this patent is extended or adjusted under 35 U.S.C. 154(b) by 372 days.

(21) Appl. No.: 16/833,992

(22) Filed: Mar. 30, 2020

(65) Prior Publication Data

US 2020/0308316 A1    Oct. 1, 2020

Related U.S. Application Data

(60) Provisional application No. 62/827,401, filed on Apr. 1, 2019.

(51) Int. Cl.
*C07C 2/08* (2006.01)
*C07C 2/32* (2006.01)
(Continued)

(52) U.S. Cl.
CPC .............. *C08F 4/7098* (2013.01); *C07C 2/08* (2013.01); *C07C 2/32* (2013.01); *C08F 10/14* (2013.01)

(58) Field of Classification Search
CPC .................................... C07C 2/08; C07C 2/32
See application file for complete search history.

(56) References Cited

U.S. PATENT DOCUMENTS 3,036,003 A    5/1962    Verdol
3,172,892 A    3/1965    Le Suer et al.
(Continued)

FOREIGN PATENT DOCUMENTS

EP          1040115 B1    6/2004
JP       2000169401 A    6/2000
(Continued)

OTHER PUBLICATIONS

Wang et al., "Chain-Walking Polymerization of Linear Internal Octenes Catalyzed by alpha-Diimine Nickel Complexes", Organometallics, vol. 37 (2018), pp. 1358-1367.
(Continued)

*Primary Examiner* — Caixia Lu
(74) *Attorney, Agent, or Firm* — C. Tumey Law Group PLLC

(57) ABSTRACT

The present disclosure provides base stocks and or diesel fuel, and processes for producing such base stocks and or diesel fuel by polymerizing alpha-olefins and internal olefins. The present disclosure further provides polyolefin products useful as base stocks and or diesel fuel. In at least one embodiment, a process includes: i) introducing, neat or in the presence of a solvent, a feed comprising a branched $C_5$-$C_{30}$ internal olefin, with a catalyst compound comprising a group 8, 9, 10, or 11 transition metal and at least one heteroatom and ii) obtaining a $C_6$-$C_{100}$ polyolefin product having one olefin, a methylene content of from about 1 wt % to about 98 wt %, and or a methyl content of from about 1 wt % to about 75 wt %. The feed may further include a linear $C_4$-$C_{30}$ internal olefin, a $C_2$-$C_{30}$ alpha-olefin, or a mixture thereof.

24 Claims, 5 Drawing Sheets

(51) Int. Cl.
  *C08F 4/70* (2006.01)
  *C08F 10/14* (2006.01)

(56) References Cited

U.S. PATENT DOCUMENTS

| | | |
|---|---|---|
| 3,219,666 A | 11/1965 | Norman et al. |
| 3,316,177 A | 4/1967 | Dorer, Jr. |
| 4,234,435 A | 11/1980 | Meinhardt et al. |
| 4,317,948 A | 3/1982 | Heckelsberg |
| 4,533,651 A | 8/1985 | Masters et al. |
| 4,889,647 A | 12/1989 | Rowan et al. |
| 4,978,464 A | 12/1990 | Coyle et al. |
| 5,177,282 A | 1/1993 | Nierlich et al. |
| 5,545,792 A | 8/1996 | Cox |
| 5,633,418 A | 5/1997 | Sato et al. |
| 5,705,458 A | 1/1998 | Roby et al. |
| 5,852,145 A | 12/1998 | McLain et al. |
| 6,291,733 B1 | 9/2001 | Small et al. |
| 6,897,272 B1 | 5/2005 | Brookhart et al. |
| 7,056,997 B2 | 6/2006 | Small et al. |
| 8,404,880 B2 | 3/2013 | Kaji et al. |
| 8,975,209 B2 | 3/2015 | Kaji et al. |
| 9,120,989 B2 | 9/2015 | Freel et al. |
| 9,340,630 B2 | 5/2016 | Kaji et al. |
| 9,682,898 B2 | 6/2017 | Ranish et al. |
| 2007/0123659 A1 | 5/2007 | Wu et al. |
| 2013/0118059 A1 | 5/2013 | Lange et al. |
| 2013/0130952 A1 | 5/2013 | Luo et al. |
| 2014/0179964 A1 | 6/2014 | Gee |
| 2015/0166428 A1* | 6/2015 | Krupa .............. C10G 50/00 585/517 |
| 2015/0306588 A1 | 10/2015 | Boulens et al. |
| 2017/0051222 A1 | 2/2017 | Tang et al. |
| 2017/0334806 A1 | 11/2017 | Agee |
| 2018/0105478 A1 | 4/2018 | Lief et al. |
| 2020/0181295 A1* | 6/2020 | Ho .................. C08F 10/14 |

FOREIGN PATENT DOCUMENTS

| | | | |
|---|---|---|---|
| WO | WO-9847616 A1 * | 10/1998 | ......... B01J 31/0284 |
| WO | 99/31113 A1 | 6/1999 | |

OTHER PUBLICATIONS

Wang et al., "Living polymerization of higher 2-alkene with alpha-diimine nickel catalysts: Synthesis and characterization of high molecular weight poly(2-alkene)s", Polymer, Volumer 127 (2017), pp. 88-100.

Endo et al., "Polymerization of 2-Pentene with Ni(II) alpha-diimine Complex/M-MAO Catalyst and Structure of the Polymer", Journal of Polymer Science: Part A: Polymer Chemistry, vol. 46 (2008), pp. 2858-2863.

Leatherman et al., "Ni(II)-Catalyzed Polymerization of trans-2-Butene", Macromolecules, vol. 34 (2001), pp. 2748-2750.

Liu et al., "Mechanistic Studies of Palladium(II)-alpha-Diimine-Catalyzed Polymerizations of cis- and trans-2-Butenes", Organometallics, vol. 23 (2004), pp. 6099-6107.

Cherian et al., "Chiral anilines: development of C2-symmetric, late transition metal catalysts for isoselective 2-butene polymerization", ChemComm, (2003) pp. 2566-2567.

Nicolaides et al., "Unusual regioselectivity observed in the oligomerization of propene on nickel(II) ion-exchanged silica-alumina catalysts", Supported Catalysts and Their Applications—Royal Society of Chemistry, vol. 266 (2001), pp. 226-232.

Wang et al., "Late transition metal complexes bearing 2,9-bis(imino)-1,10-phenanthrolinyl ligands: synthesis, characterization and their ethylene activity", Journal of Organometallic Chemistry, vol. 658 (2002), pp. 62-70.

O'Connor et al., "Understanding the Insertion Pathways and Chain WalkingMechanisms of α-Diimine Nickel Catalysts for α-Olefin Polymerization: A 13C NMR Spectroscopic Investigation", Macromolecules, vol. 50 (2017), pp. 7010-7027.

Gao et al., "Oligomerization of 1-butene. III. Catalyst system containing nickel p-toluene sulfonate and nickel polystyrene sulfonate", Fenzi Cuihua, vol. 2 (1988), pp. 101-107.

Cao et al., "Oligomerization reaction of 1-butenes. (IX). Oligomerization reaction mechanism in nickel carboxylate/ethylaluminum chloride system", Gaodeng Xuexiao Huaxue Xuebao, vol. 14 (1993), pp. 1600-1604.

Cai et al., "Propene oligomerization catalyst derived from nickel sulfate supported on gamma-alumina", Applied Catalysis, vol. 69 (1991), pp. 1-13.

Munshieva, "Oligomerization of ethylene in the presence of some complexes of nickel with phosphorous hexaethyltriamide", Zhurnal Prikladnoi Khimii, vol. 70 (1997), pp. 327-329.

Titova et al., "Catalysis of dimerization and oligomerization reactions of lower alkenes by systems based on Ni (PPh3)2(C2H4) and Ni(PPh3)nCl (n=2 or 3)", Kinetics and Catalysis, vol. 55 (2014), pp. 35-46.

Foulds et al., "Catalytic olefin oligomerization activity of a series of trialkyl- and triphenylphosphine derivatives of the nickel(II) complexes of 4-thioxo-2-pentanoate and 2,4-pentanedithionate", Journal of Molecular Catalysis, vol. 87 (1994), pp. 117-136.

Sakakibara et al., "Oligomerization of olefins by nickel complexes. IV. Oligomerization of ethylene in the presence of bis(acetylacetonato)nickel(II) triethyldialuminum trichloride triphenylphosphine catalysts. Formation of C6-olefins", Nippon Kagaku Kaishi, vol. 5 (1974), pp. 910-914.

Brueckner et al., "The role of different Ni sites in supported nickel catalysts for butene dimerization under industry-like conditions", Journal of Catalysis, vol. 266 (2009), pp. 120-128.

Gehrke et al., "Complex catalysis. XXVI. Catalysis of the oligomerization of ethylene by cationic allylbis-ligand-nickel (II) hexafluorophosphate complexes", Journal of Organometallic Chemistry, vol. 304 (1986), pp. C4-C6.

Rishina et al., "New .alpha.-diimine nickel complexes—Synthesis and catalysis of alkene oligomerization reactions", Journal of Molecular Catalysis A: Chemical, vol. 423 (2016), pp. 495-502.

Lutz, "Shell Higher Olefin Process", Journal of Chemical Education, vol. 1986, pp. 202-203.

Song et al., "Ionic liquid-supported bis-(salicylaldimine) nickel complexes: robust and recyclable catalysts for ethylene oligomerization in biphasic solvent system", Catalysis Letters, vol. 131 (2009), pp. 566-573.

Gao et al., "Living/controlled polymerization of 4-methyl-1-pentene with α-diimine nickel-diethylaluminium chloride: effect of alkylaluminium cocatalysts", Polymer Chemistry, vol. 2 (2011), pp. 1398-1403.

Nelkenbaum et al., "Synthesis and Molecular Structures of Neutral Nickel Complexes. Catalytic Activity of (Benzamidinato)(acetylacetonato)nickel for the Addition Polymerization of Norbornene, the Oligomerization of Ethylene, and the Dimerization of Propylene", Organometallics, vol. 24 (2005), pp. 2645-2659.

Behr et al., "Highly Selective Dimerization and Trimerization of Isobutene to Linearly Linked Products by Using Nickel Catalysts", Chemistry—An Asian Journal, vol. 9 (2014), pp. 596-601.

Bennett et al., "Synthesis of heterogeneous olefin-oligomerization catalysts using homogeneous nickel-chelate complexes as a basis", Polyhedron, vol. 9 (1990), pp. 2823-2831.

Brunet et al., "Cationic (μ3-allyl)metal complexes: Part XIV1. catalytic oligomerisation of ethylene: a very selective dbmerisation catalyst prepared from [(μ3-methallyl)ni(cod)]pf6 and a tris(3-sulphophenyl)-phosphine salt", J. Mol. Catalysis, vol. 50 (1989), pp. 291-302.

Rossetto et al., "Heterogeneous complexes of nickel MCM-41 with β-diimine ligands: Applications in olefin oligomerization", J. Catalysis, vol. 323 (2015), pp. 45-54.

Borba et al., "β-Diimine nickel complexes in BMI•AlCl4 ionic liquid: a catalytic biphasic system for propylene oligomerization", Applied Catalysis A, vol. 538 (2017), pp. 51-58.

(56) References Cited

OTHER PUBLICATIONS

Alt et al., "Catalytic Dimerization of Propene with Diiminophosphorane Nickel (II) Complexes in the Presence of Phosphine Additives", Jordan J. of Chemistry, vol. 3 (2008), pp. 367-379.

Poorters et al., "Synthesis and Properties of TRANSDIP, a Rigid Chelator Built upon a Cyclodextrin Cavity: Is TRANSDIP an Authentic trans-Spanning Ligand?", Chemistry—A European Journal, vol. 13 (2007), pp. 9448-9461.

Milinar et al., "The Effect of Noncatalytic Cations on the Activity and Selectivity of Nickel-Exchanged X Zeolites for Propene Oligomerization", ChemCatChem, vol. 5 (2013), pp. 3139-3147.

Axenov et al., "Bis(imino)cyclodiphosph(V)azane complexes of late transition metals: Efficient catalyst precursors for ethene and propene oligomerization and dimerization", J. of Catalysis, vol. 238 (2006), pp. 196-205.

Cai et al., "Customizing Polyolefin Morphology by Selective Pairing of Alkali Ions with Nickel Phenoxyimine-Polyethylene Glycol Catalysts", Organometallics, vol. 36 (2017), pp. 4691-4698.

Nyamoto et al., "Unsymmetrical (pyrazolylmethyl)pyridine metal complexes as catalysts for ethylene oligomerization reactions: Role of solvent and co-catalyst in product distribution", J. Mol. Catalysis A, vol. 394 (2014), pp. 274-282.

Zhang et al., "Synthesis of Branched Polyethylene Using (alpha-Diimine)Nickel(II)-TiCl4 Combined and Supported Catalyst", Chinese Journal of Polymer Science, vol. 22 (2004), pp. 313-319.

Deimund et al., "Nickel-Exchanged Zincosilicate Catalysts for the Oligomerization of Propylene", ACS Catalysis, vol. 4 (2014), pp. 4189-4195.

Olivier-Bourbigou, et al., "Ionic Liquids and Catalysis: the IFP Biphasic Difasol Process", Green Catalysis, vol. 1: Homogeneous Catalysis (2009), pp. 101-126.

Beach, et al., "Linear Dimerization of Propylene and 1-Butene Catalyzed By (n3-4-Cyclooctene-1-YL)-(1,1,1,5,5,5-Hexafluoro-2, 4 Pentandedionato) Nickel", Journal of Molecular Catalysis, vol. 34 (1986), pp. 345-354.

Keim, "Nickel: An Element With Wide Application In Industrial Homogeneous Catalysis", Angew. Chem. Int. Ed. Engl. 29 (1990), pp. 235-244.

Behr, et al., "Oligomerization of 1-butene with a Homogeneous Catalyst System Based on Allylic Nickel Complexes", The Royal Society of Chemistry, vol. 5 (2015) pp. 41372-41376.

Olivier-Bourbigou, "Ionic Liquids: New Solvents and Technology for More Environmentally Friendly Processes", Innovation Energy Environment, 2007, pp. 1-26.

The International Search Report and Written Opinion of PCT/2020/025664 dated Jun. 17, 2020.

* cited by examiner

PROCESSES FOR POLYMERIZING ALPHA-OLEFINS, INTERNAL OLEFINS AND COMPOSITIONS THEREOF

CROSS-REFERENCE TO RELATED APPLICATIONS

This application claims priority to U.S. Provisional Application No. 62/827,401 filed Apr. 1, 2019, which is herein incorporated by reference in its entirety.

FIELD

The present disclosure provides processes for polymerizing low molecular weight alpha-olefins, linear internal olefins, and branched internal olefins. The present disclosure further provides polyolefin products useful as diesel fuel, and or base stocks, and or chemical intermediates.

BACKGROUND

The polymerization (e.g., oligomerization) of light monoolefins offers an attractive way for upgrading light olefins to produce either, fuel components (e.g., gasoline; middle distillates), which are commonly branched, or as intermediates for the manufacture of various types of products targeted in the petrochemical industry. Highly linear products are desirable in the fuel industry (e.g., feedstocks for diesel blending due to high cetane values). Branched alcohol production is desirable for the synthesis of surfactants, polymer additives, lube and fuel additives, adhesives, and other industrial products).

Commercial processes for butenes oligomerization using homogeneous catalysts in a liquid phase (e.g., Dimersol process), heterogeneous catalysts (e.g., Octol process), or ionic liquid catalyst solvents (e.g., Difasol process) are in constant development, seeking for more performant catalyst systems and conditions (e.g., temperature, time, recycling solvents, recycling catalysts, feed impurities tolerance) that would satisfy the increased demand of "higher olefins", which are also referred to as reactive intermediates, used to manufacture products (e.g., lube oil additives, surfactants, agricultural chemicals, coatings, corrosion inhibitors, feedstocks for alcohols, plasticizers, and neodecanoic acids), in the petrochemical industry.

Diesel fuel is one of the major transportation fuels. Diesel fuel is a mixture of many different hydrocarbons with the carbon numbers ranging, for example, from 8 to 25. Usually, n-alkanes and oxygenates (e.g., ethers) in diesel fuel tend to increase the cetane number, while branched or unsaturated hydrocarbons lower the cetane number value. Hydrogenated polyolefin products can be used as diesel fuels having a high cetane number, if the polyolefins are less branched. A high-cetane diesel fuel provides, for example, more complete combustion, improved cold starts, less engine noise and knocking, reduced white smoke and warm-up time, and lower exhaust emissions (e.g., hydro carbon, carbon monoxide, and sometimes particulate matter), as compared to diesel fuels having lower cetane numbers.

In addition, higher olefins are reactive intermediates used to manufacture products used in lube oil additives, surfactants, agricultural chemicals, coatings and corrosion inhibitors. Base stocks are a key enabler for formulating high-quality lubricants to help meet today's energy efficiency, emission reduction and fuel economy challenges. Base stock is a constituent in finished lubricants and the characteristics of the base stock contribute to the properties of the finished lubricants. Finished lubricants include engine oils, crankcase lubricants, fiber optic cable, food-grade processing lubricants and greases, and various industrial lubricants. Lubricants in actual commercial use are prepared from a variety of natural and synthetic base stocks admixed with various additive packages and solvents depending upon their intended application. The base stocks typically include mineral oils, polyalphaolefins (PAO), gas-to-liquid base oils (GTL), silicone oils, phosphate esters, diesters, polyol esters, and the like.

Base stocks are categorized according to the American Petroleum Institute (API) classifications based on saturated hydrocarbon content, sulfur level, and viscosity index (see Table 1 infra). Typically, Group I, II, and III base stocks are each derived from crude oil via extensive processing, such as fractionating, solvent extraction, solvent dewaxing, and hydroisomerization. Group III base stocks can also be produced from synthetic hydrocarbon liquids obtained from natural gas, coal, or other fossil resources. Group IV base stocks are polyalphaolefins (PAOs), and are produced by the oligomerization of alpha olefins. Group V base stocks include all base stocks that do not belong to Groups I-IV, such as naphthenics, polyalkylene glycols (PAG), alkyl aromatics and esters.

Additionally, there are the informal categories of base stocks referred to as "Group II+" and "Group III+" that are generally recognized within the lubricant industry as corresponding to base stocks that exceed the minimum classification requirements of the formal group. For example, a "Group II+" base stock may have a viscosity index (VI) above 110 and a "Group III+" base stock may have a viscosity index (VI) between 130 and 150.

TABLE 1

| | API Classification | | | | |
|---|---|---|---|---|---|
| Property | Group I | Group II | Group III | Group IV | Group V |
| % Saturates | <90 | ≥90 | ≥90 | Polyalpha-olefins (PAOs) | All others not belonging to group I-IV |
| % Sulfur | >0.03 | ≤0.03 | ≤0.03 | | |
| Index (VI) | 80-120 | 80-120 | ≥120 | | |

Group IV PAOs, for example, can be synthesized by cationic oligomerization with a Lewis acid catalyst, such as $BF_3$, using 1-decene as feedstock followed by hydrogenation of the obtained oligomers. Furthermore, polymerization of $C_3$ and higher alpha-olefins can be performed using early transition metal catalysts (e.g., Ti, Zr, Hf, or V). Processes using acid catalysts lead to the formation of highly branched products, such that products contain high amount of methyl branches, as determined by $^{13}C$ NMR spectroscopy, which gives different product properties than the transition metal catalyzed products.

Internal olefins (e.g., linear internal olefins and branched internal olefins) on the other hand, have not been utilized as feed for base stock manufacturing due to their tendency to form highly branched products. Lower molecular weight internal olefins are abundantly available from a variety of refining sources such as fluid catalytic cracking (FCC) gasoline and coker naphtha. For example, 5% of FCC products are $C_5$-olefins, which represent approximately 300 KBD in the United States, and approximately 62% of those are internal olefins. Due to their low reactivity, there are currently no significant uses of these olefins as feed to make higher molecular weight products. Therefore, upgrading these feeds into higher value products would be desirable.

However, value upgrade options of the internal olefins are typically limited to alkane alkylation to gasoline and oligomerization to chemical intermediates, both promoted by acid catalysts.

Nonetheless, higher linearities of products, by means of linear hydrocarbons, are more desirable for a wide range of applications, such as precursors for plasticizers, diesel, and jet fuel.

There is a need for processes for polymerizing low molecular weight alpha-olefins and internal olefins, such as linear and branched olefins, that can provide novel linear base stocks and diesel fuel.

Furthermore, under present conditions, petroleum refineries are finding it increasingly necessary to seek the most cost-effective means of improving the quality of diesel fuel products. Cetane number is a measure of ignition quality of diesel fuels. Cetane number is highly dependent on the paraffinicity of molecular structures whether they are straight chains or alkyl attachments to the rings. Distillate aromatic content, for example, is inversely proportional to cetane number while a high paraffinic content is directly proportional to a high cetane number. Fuels including less branching materials also have higher cetane number.

In light of the ever present need for improving conventional diesel formation processes and for improving diesel fuel properties, there remains a need for processes of obtaining diesel fuel with high cetane number that can be formed from alpha-olefins and internal olefins.

References for citing in an Information Disclosure Statement (37 C.F.R. 1.97(h)): Behr, A.; Rentmeister, N.; Seidensticker, T.; Vosberg, J.; Peitz. S.; Maschmeyer, D. "Highly Selective Dimerization and Trimerization of Isobutene to Linearly Linked Products by Using Nickel Catalysts" *Chem. Asia. J.* 2014, 9. pp. 556-601; Keim, W. "Nickel: an Element with Wide Application in Industrial Homogeneous Catalysis" *Angew. Chem. Int. Ed. Engl.* 1990, 29, pp. 235-244; Behr, A.; Bayrak, Z.; Peitz, S.; Stochniol, G.; Maschmeyer, D. "Oligomerization of 1-butene with a Homogeneous Catalyst System Based on Allylic Nickel Complexes" *RSC Adv.* 2015, 5, pp. 41372-41376; U.S. Pat. Nos. 9,682,898; 5,177, 282; Olivier-Bourbigou, H.; Favre, F.; Forestière, A.; Hugues, F. "Ionic Liquids and Catalysis: the IFP Biphasic Difasol Process" Handbook of Green Chemistry, book chapter 2010; Olivier-Bourbigou, H. "Ionic Liquids: New Solvents and Technology for More Environmentally Friendly Processes", IFP Innovation Energy Environment, 2007.

SUMMARY

The present disclosure provides diesel fuel, base stocks, and or chemical intermediates, and processes for producing such diesel fuel, base stocks and or chemical intermediates by polymerizing $C_2$-$C_{30}$ alpha-olefins, linear $C_4$-$C_{30}$ internal olefins, branched $C_5$-$C_{30}$ internal olefins, or mixture thereof. The present disclosure further provides polyolefin products useful as diesel fuel. The present disclosure further provides diesel fuel and or base stocks, comprising low molecular weight polyolefin products.

In at least one embodiment, a process includes: i) introducing, neat or in the presence of a solvent, a feed comprising a branched $C_5$-$C_{30}$ internal olefin with a catalyst compound comprising a group 8, 9, 10, or 11 transition metal and at least one heteroatom; and ii) obtaining a $C_6$-$C_{100}$ polyolefin product having one olefin, a methylene content of from about 1 wt % to about 98 wt %, based on the total weight of the $C_6$-$C_{100}$ polyolefin product, and or a methyl content of from about 1 wt % to about 75 wt %, based on the total weight of the $C_6$-$C_{100}$ polyolefin product. The feed may further comprise a linear $C_4$-$C_{30}$ internal olefin, a $C_2$-$C_{30}$ alpha-olefin, or a mixture thereof.

A process of the present disclosure may include: i) introducing, neat or in the presence of a solvent, a feed comprising a branched $C_5$-$C_{30}$ internal olefin with a catalyst system comprising (1) a catalyst comprising a group 8, 9, 10, or 11 transition metal and at least one heteroatom, (2) an activator, and (3) optionally a support material; and ii) obtaining a $C_6$-$C_{100}$ polyolefin product. The feed further comprises a linear $C_4$-$C_{30}$ internal olefin, a $C_2$-$C_{30}$ alpha-olefin, or a mixture thereof.

In at least one embodiment, a $C_6$-$C_{100}$ polyolefin product has one olefin, as determined by $^1$H NMR spectroscopy.

A process of the present disclosure may further include hydrogenating the $C_6$-$C_{100}$ polyolefin product to form a $C_6$-$C_{100}$ hydrogenated polyolefin product. In at least one embodiment, the $C_6$-$C_{100}$ hydrogenated polyolefin product has one or more of: a cetane number of about 30 or greater, a methylene content of from about 1 wt % to about 98 wt % (based on the total weight of the $C_6$-$C_{100}$ hydrogenated polyolefin product, as determined by GC measurements), and or a methyl content of from about 1 wt % to about 75 wt % (based on the total weight of the $C_6$-$C_{100}$ hydrogenated polyolefin product, as determined by GC measurements).

DETAILED DESCRIPTION

Figure 1:
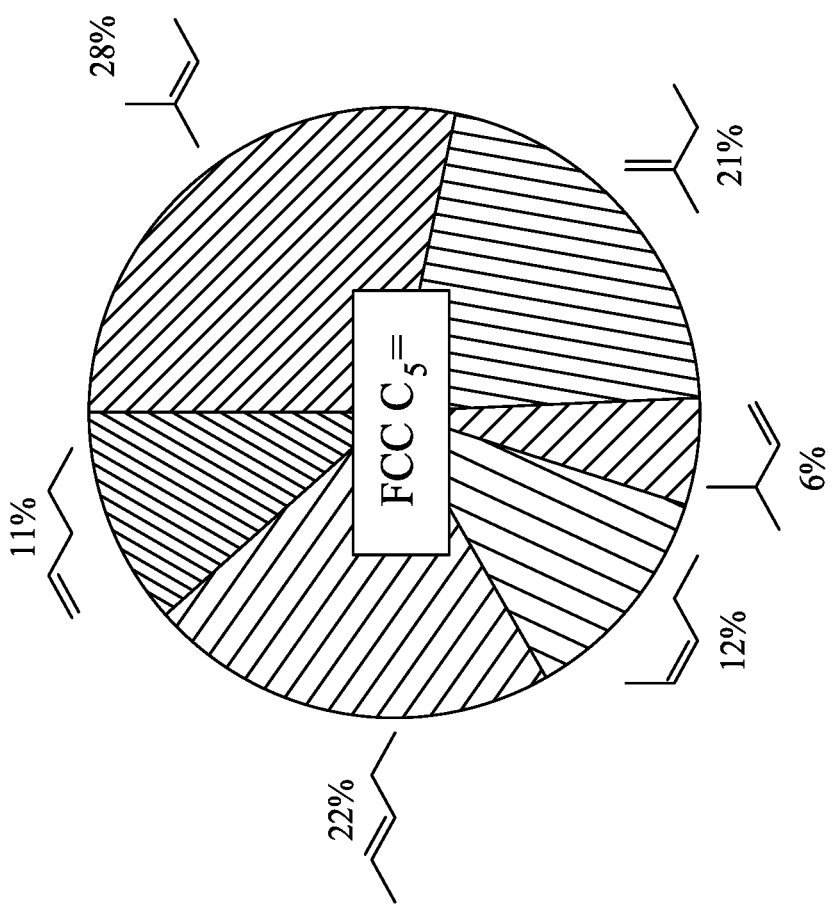
FIG. 1 is a pie chart illustrating $C_5$-olefin content (%) of the products formed by Fluid Catalytic Cracking (FCC), according to one embodiment.

The present disclosure provides novel low-branched diesel fuel, base stocks, and or chemical intermediates, and processes for producing such diesel fuel, base stocks, and or chemical intermediates by polymerizing low molecular weight alpha-olefins and or internal olefins and or branched olefins. In one aspect, a light distillate product includes one or more C6-C100 hydrocarbon product(s). The light distillate product may be blended with one or more other components (e.g., additives) to produce, for example, a fuel composition (e.g., higher value diesel (cetane)), waxes, lubricant range products, and base stocks. The present disclosure further provides polyolefin products (e.g., linear base stocks, diesel fuel) having one or more of improved flow, low temperature properties, and thickening efficiency. The present disclosure further provides novel diesel compositions and processes for producing such diesel compositions by polymerizing low molecular weight alpha-olefins and internal olefins.

In at least one embodiment, a process includes: i) introducing, neat or in the presence of a solvent, a feed comprising a branched $C_5$-$C_{30}$ internal olefin with a catalyst compound comprising a group 8, 9, 10, or 11 transition metal and at least one heteroatom (e.g., fluorine); and ii) obtaining a $C_6$-$C_{100}$ polyolefin product having one olefin, a methylene content of from about 1 wt % to about 98 wt %, based on the total weight of the $C_6$-$C_{100}$ polyolefin product, and or a methyl content of from about 1 wt % to about 75 wt %, based on the total weight of the $C_6$-$C_{100}$ polyolefin product. The feed may further comprise a linear $C_4$-$C_{30}$ internal olefin, a $C_2$-$C_{30}$ alpha-olefin, or a mixture thereof.

A process of the present disclosure may include: i) introducing, neat or in the presence of a solvent, a feed comprising a branched $C_5$-$C_{30}$ internal olefin with a catalyst system comprising (1) a catalyst comprising a group 8, 9, 10, or 11 transition metal and at least one heteroatom (e.g., fluorine), (2) an activator, and (3) optionally a support material; and ii) obtaining a $C_6$-$C_{100}$ polyolefin product. The feed further comprises a linear $C_4$-$C_{30}$ internal olefin, a $C_2$-$C_{30}$ alpha-olefin, or a mixture thereof.

In at least one embodiment, a $C_6$-$C_{100}$ polyolefin product has one olefin, a methylene content of from about 1 wt % to about 98 wt %, based on the total weight of the $C_6$-$C_{100}$ polyolefin product, and or a methyl content of from about 1 wt % to about 75 wt %, based on the total weight of the $C_6$-$C_{100}$ polyolefin product, as determined by $^1$H NMR spectroscopy.

A process of the present disclosure may further include hydrogenating the $C_6$-$C_{100}$ polyolefin product to form a $C_6$-$C_{100}$ hydrogenated polyolefin product. In at least one embodiment, the $C_6$-$C_{100}$ hydrogenated polyolefin product has one or more of a cetane number of about 30 or greater, a methyl content of from about 1 wt % to about 75 wt % (based on the total weight of the $C_6$-$C_{100}$ hydrogenated polyolefin product, as determined by GC measurements), and or a methylene content of from about 1 wt % to about 98 wt % (based on the total weight of the $C_6$-$C_{100}$ hydrogenated polyolefin product, as determined by GC measurements).

In at least one embodiment, a process of the present disclosure includes using a catalyst represented by Formula (I):

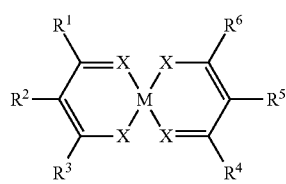

wherein:
M is a group 8, 9, 10, or 11 metal;
each X is an heteroatom; and
each of $R^1$, $R^2$, $R^3$, $R^4$, $R^5$, and $R^6$ is independently selected from hydrogen, $C_1$-$C_{40}$ hydrocarbyl, $C_1$-$C_{40}$ substituted hydrocarbyl, a heteroatom or a heteroatom-containing group, wherein at least one of $R^1$, $R^2$, $R^3$, $R^4$, $R^5$, and $R^6$ is a heteroatom or a heteroatom-containing group, or one or more of $R^1$ and $R^2$, $R^2$ and $R^3$, $R^4$ and $R^5$, or $R^5$ and $R^6$ are joined to form one or more substituted hydrocarbyl rings, unsubstituted hydrocarbyl rings, substituted heterocyclic rings, or unsubstituted to heterocyclic rings each having 5, 6, 7, or 8 ring atoms, wherein at least one of the rings is substituted with a heteroatom or a heteroatom-containing group if the remainder of R groups of Formula (I) are not a heteroatom or a heteroatom-containing group. Alternatively or additionally, each of $R^1$, $R^2$, $R^3$, $R^4$, $R^5$, and $R^6$ is independently selected from hydrogen, $C_1$-$C_{40}$ hydrocarbyl, $C_1$-$C_{40}$ substituted hydrocarbyl, a heteroatom or a heteroatom-containing group, wherein at least one of $R^1$, $R^2$, $R^3$, $R^4$, $R^5$, and $R^6$ is hydrogen or $C_1$-$C_{40}$ hydrocarbyl.

Furthermore, the ability to utilize the low activity internal and branched olefins of conventional feeds while at the same time increasing the linearity of the products has the benefit of low feed cost, improved upgrading of feeds that are mixtures of different kinds of olefins, and superior product performance.

In at least one embodiment, a base stock is a $C_6$-$C_{100}$ polyolefin product, such as a $C_{25}$-$C_{50}$ polyolefin product. In at least one embodiment, a base stock is a hydrogenated $C_6$-$C_{100}$ polyolefin product, such as a hydrogenated $C_{25}$-$C_{50}$ polyolefin product.

In at least one embodiment, a diesel fuel is a $C_6$-$C_{100}$ hydrogenated polyolefin product, such as a $C_9$-$C_{25}$ hydrogenated polyolefin product.

All numerical values within the detailed description and the claims herein are modified by "about" or "approximately" the indicated value, and take into account experimental error and variations that would be expected by a person of ordinary skill in the art.

For purposes herein, the numbering scheme for the Periodic Table Groups is used as described in CHEMICAL AND ENGINEERING NEWS, 63(5), pg. 27 (1985). For example, a "Group 4 metal" is an element from Group 4 of the Periodic Table, e.g., Hf, Ti, or Zr.

The following abbreviations may be used herein: Me is methyl, Et is ethyl, Ni(acac)$_2$ is Nickel(II) acetylacetonate, Ni(hfacac)$_2$ is Ni(II) hexafluoroacetylacetone, MAO is methylaluminoxane, RT is room temperature (and is 23° C. unless otherwise indicated), wt % is weight percent. MOFs is metal organic frameworks, BDC is 1,4-benzenedicarboxylate, VI is viscosity index, VM is viscosity modifier, TE is Thickening efficiency, TON is Turn-Over Number.

A "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers.

As used herein, the term "base stock" means a hydrocarbon liquid useable as a major component of a lubricating oil. As used herein, the term "base oil" refers to a blend of base stocks useable as a major component of a lubricating oil. As used herein, the term "major component" means a component present in a lubricating oil in an amount of about 50 weight percent (wt %) or greater. As used herein, the term "minor component" means a component (e.g., one or more lubricating oil additives) present in a lubricating oil in an amount less than about 50 wt %.

As used herein, a "catalyst" can have isomeric forms such as conformational isomers or configurational isomers. Conformational isomers include, for example, conformers and rotamers. Configurational isomers include, for example, stereoisomers.

A "catalyst system" includes at least one catalyst compound and at least one activator. When "catalyst system" is used to describe such the catalyst compound/activator combination before activation, it means the unactivated catalyst complex (precatalyst) together with an activator. When it is used to describe the combination after activation, it means the activated complex and the activator. The catalyst compound may be neutral as in a precatalyst, or a charged species with a counter ion as in an activated catalyst system.

"Conversion" is the amount of monomer that is converted to polymer product, and the conversion reported herein is defined as the amount of monomer fed into the reactor that is converted divided by total amount of monomer fed into the reactor.

"Catalyst activity" is a measure of the level of activity of the catalyst and is reported as the number of moles of the feed reacted per moles of catalyst used, and is also referred to as the turn-over number (TON).

Unless otherwise indicated, (e.g., the definition of "substituted hydrocarbyl", "substituted aromatic", etc.), the term "substituted" means that at least one hydrogen atom has been replaced with at least one non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, —(CH$_2$)q-SiR*$_3$, where q is 1 to 10 and each R* is independently a hydrocarbyl or halocarbyl radical, and two or more R* may join together to form a substituted or unsubstituted to completely saturated, partially unsaturated, or aromatic cyclic or polycyclic ring structure), or where at least one heteroatom has been inserted within a hydrocarbyl ring.

The term "substituted hydrocarbyl" means a hydrocarbyl radical in which at least one hydrogen atom of the hydrocarbyl radical has been substituted with at least one heteroatom (such as halogen, e.g., Br, Cl, F or I) or heteroatom-containing group (such as a functional group, e.g., —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, —(CH$_2$)q-SiR*$_3$, where q is 1 to 10 and each R* is independently a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring. The term "hydrocarbyl substituted phenyl" means a phenyl group having 1, 2, 3, 4 or 5 hydrogen groups replaced by a hydrocarbyl or substituted hydrocarbyl group. For example, the "hydrocarbyl substituted phenyl" group can be represented by the formula:

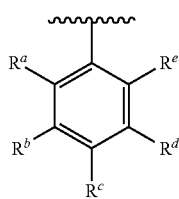

where each of $R^a$, $R^b$, $R^c$, $R^d$, and $R^e$ can be independently selected from hydrogen, $C_1$-$C_{40}$ hydrocarbyl or $C_1$-$C_{40}$ substituted hydrocarbyl, a heteroatom or a heteroatom-containing group (provided that at least one of $R^a$, $R^b$, $R^c$, $R^d$, and $R^e$ is not H), or two or more of $R^a$, $R^b$, $R^c$, $R^d$, and $R^e$ can be joined together to form a $C_4$-$C_{62}$ cyclic or polycyclic hydrocarbyl ring structure, or a combination thereof.

The term "substituted aromatic," means an aromatic group having 1 or more hydrogen groups replaced by a hydrocarbyl, substituted hydrocarbyl, heteroatom or heteroatom containing group.

The term "substituted phenyl," mean a phenyl group having 1 or more hydrogen groups replaced by a hydrocarbyl, substituted hydrocarbyl, heteroatom or heteroatom containing group.

The term "substituted carbazole," means a carbazolyl group having 1 or more hydrogen groups replaced by a hydrocarbyl, substituted hydrocarbyl, heteroatom or heteroatom containing group.

The term "substituted naphthyl," means a naphthyl group having 1 or more hydrogen groups replaced by a hydrocarbyl, substituted hydrocarbyl, heteroatom or heteroatom containing group.

The term "substituted anthracenyl," means an anthracenyl group having 1 or more hydrogen groups replaced by a hydrocarbyl, substituted hydrocarbyl, heteroatom or heteroatom containing group.

The term "substituted fluorenyl" means a fluorenyl group having 1 or more hydrogen groups replaced by a hydrocarbyl, substituted hydrocarbyl, heteroatom or heteroatom containing group.

The terms "alkoxy" and "alkoxide" mean an alkyl or aryl group bound to an oxygen atom, such as an alkyl ether or aryl ether group/radical connected to an oxygen atom and can include those where the alkyl/aryl group is a $C_1$ to $C_{10}$ hydrocarbyl. The alkyl group may be straight chain, branched, or cyclic. The alkyl group may be saturated or unsaturated. Examples of suitable alkoxy radicals can include methoxy, ethoxy, n-propoxy, iso-propoxy, n-butoxy, iso-butoxy, sec-butoxy, tert-butoxy, phenoxy.

The term "alkenyl" means a straight-chain, branched-chain, or cyclic hydrocarbon radical having one or more double bonds. These alkenyl radicals may be optionally substituted. Examples of suitable alkenyl radicals can include ethenyl, propentyl, allyl, 1,4-butadienyl cyclopropentyl, cyclobutenyl, cyclopentenyl, cyclohexenyl, cyclooctenyl, including their substituted analogues.

The terms "alkyl radical," and "alkyl" are used interchangeably throughout this disclosure. For purposes of this disclosure. "alkyl radical" is defined to be $C_1$-$C_{100}$ alkyls, that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, including their substituted analogues. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, or —(CH$_2$)—SiR*$_3$, and each R* is independently a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring.

The term "aryl" or "aryl group" means an aromatic ring and the substituted variants thereof, such as phenyl, 2-methyl-phenyl, xylyl, 4-bromo-xylyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom-substituted ring.

The terms "hydrocarbyl." "hydrocarbyl group," or "hydrocarbyl radical" may be used interchangeably and are defined to mean a group consisting of hydrogen and carbon atoms only. For example, a hydrocarbyl can be a $C_1$-$C_{100}$ radical that may be linear, branched, or cyclic, and when cyclic, aromatic or non-aromatic. Examples of such radicals may include, but are not limited to, alkyl groups such as methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and aryl groups, such as phenyl, benzyl naphthyl.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic. The term "olefin" can be alternatively referred to as "alkene". An olefin can be substituted or unsubstituted.

The term "terminal olefin", also referred to as "alpha-olefin", refers to an olefin having a terminal carbon-to-carbon double bond in the structure thereof (($R^xR^y$)—C=$CH_2$, where $R^x$ and $R^y$ can be independently hydrogen or any hydrocarbyl group, such as $R^x$ is hydrogen, and $R^y$ is an alkyl group). In other words, an "alpha-olefin" is an olefin having a double bond at the alpha (or 1-) position. A "linear terminal olefin" is a terminal olefin defined in this paragraph wherein $R^x$ is hydrogen, and $R^y$ is hydrogen or a linear alkyl group. As used herein, terms "linear terminal olefin" and "linear alpha-olefin" are used interchangeably. A "linear alpha-olefin" or "LAO" is an olefin with a double bond at the alpha position and a linear hydrocarbon chain. A "poly (alpha-olefin)" or "PAO" is a polymer having two or more alpha-olefin units. As used herein, terms "poly(alpha-olefin)" and "poly(alpha-olefin) polymer" are used interchangeably. For the purposes of this disclosure, the term "α-olefin" includes $C_2$-$C_{20}$ olefins. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

For purposes of this disclosure, ethylene shall be considered an alpha-olefin (also referred to as an "α-olefin").

The term "alpha-olefin" includes vinylogous compounds. The term "vinyl" means an olefin having the following formula:

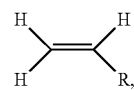

wherein R is a hydrocarbyl group, such as a saturated hydrocarbyl group.

The term "internal olefin" includes olefins that are vinylenes.

The term "linear olefins" includes 1,1-disubstituted olefins and linear internal olefins, such as 1,2-di-substituted olefins. The term "1,1-di-substituted olefin" includes "vinylidene". The term "vinylidene" means an olefin having the following formula:

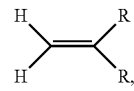

wherein each instance of R is independently a hydrocarbyl group, such as a saturated hydrocarbyl group. The term 1,2-di-substituted olefin includes "vinylene" or "1,2-di-substituted vinylene" means:
(i) an olefin having the following formula (which is a "cis-" conformation):

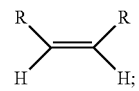

(ii) an olefin having the following formula (which is a "trans-" conformation):

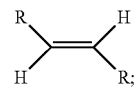

or (iii) a mixture of (i) and (ii) at any proportion thereof, wherein each instance of R is independently a hydrocarbyl group, such as saturated hydrocarbyl group.

The term "branched olefin" includes branched internal olefins such as "tri-substituted olefin". The term "tri-substituted olefin" includes tri-substituted vinylene. The term "tri-substituted vinylene" means an olefin having the following formula:

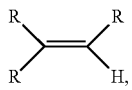

wherein each instance of R is independently a hydrocarbyl group, such as a saturated hydrocarbyl group.

Alpha-Olefins

An alpha-olefin (e.g., monomers) of the present disclosure can be a linear or branched $C_2$-$C_{30}$ olefin. Monomers can include substituted or unsubstituted $C_2$ to $C_{30}$ alpha olefins, such as substituted or unsubstituted $C_2$ to $C_{20}$ alpha olefins, such as substituted or unsubstituted $C_2$ to $C_{12}$ alpha olefins, such as ethylene, propylene, 1-butene, 2-methyl-1-propene, 1-pentene, 2-methyl-1-butene, 3-methyl-1-butene, 1-hexene, 2-methyl-1-pentene, 2-ethyl-1-butene, 3-methyl-1-pentene, 4-methyl-1-pentene, heptene, octene, nonene, decene, undecene, dodecene and isomers thereof. In at least one embodiment, a substituted and or unsubstituted alpha-olefin is selected from one or more of 1-butene, 1-pentene, 1-hexene, 1-heptene, 1-octene, 1-nonene, 1-decene.

Internal Olefins

An internal olefin (e.g., monomers) of the present disclosure can be a linear $C_4$-$C_{30}$ olefin, a branched $C_5$-$C_{30}$ olefin, or a cyclic $C_4$-$C_{30}$ olefin, having one or more carbon-carbon double bonds along the olefin backbone (also referred to as "internal unsaturation") instead of, or in addition to, a carbon-carbon double bond at a terminus of the olefin (also referred to as "terminal unsaturation"). Linear $C_4$-$C_{30}$ internal olefins or branched $C_5$-$C_{30}$ internal olefins may be referred to as $C_4$-$C_{30}$ internal olefins. In addition to internal unsaturations, a $C_4$-$C_{30}$ internal olefin may additionally have one or more terminal unsaturations. An internal olefin can have one or more cis-conformations or one or more trans-conformations. The monomers may include one or more $C_4$ to $C_{30}$ cyclic olefins, such as $C_4$ to $C_{20}$ cyclic olefins, such as $C_6$ to $C_{12}$ cyclic olefins. The $C_4$ to $C_{30}$ cyclic olefins may be strained or unstrained, monocyclic or polycyclic, and may optionally include heteroatoms and or one or more functional groups.

In at least one embodiment, an internal olefin is selected from a cis-configuration, trans-configuration, or mixture thereof of one or more of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, and 5-decene.

Exemplary $C_4$ to $C_{30}$ internal olefin monomers may also include, norbornene, cyclopentene, cyclohexene, cycloheptene, cyclooctene, cyclododecene, 7-oxanorbornene, substituted derivatives thereof, and isomers thereof, such as 1-hydroxy-4-cyclooctene, 1-acetoxy-4-cyclooctene, 5-methylcyclopentene and their respective homologs and derivatives.

Internal olefins of the present disclosure can be obtained from commercial sources (such as Sigma Aldrich or TCI) and or may be obtained from refined hydrocarbon feeds such as fluid catalytic cracking (FCC) gasoline or coker naphtha. For example, a cellulosic feed material may be liquefactioned to form a product that then undergoes a fluid catalytic cracking process, as described in U.S. Pub. No. 2013/0118059. Any suitable cellulose-containing material may be used as a cellulosic material of the present disclosure. The cellulosic material for use according to the present disclosure may be obtained from a variety of plants and plant materials including agricultural wastes, forestry wastes, sugar processing residues and or mixtures thereof. Examples of suitable cellulose-containing materials include agricultural wastes such as corn stover, soybean stover, corn cobs, rice straw, rice hulls, oat hulls, corn fiber, cereal straws such as wheat, barley, rye and oat straw, grasses, forestry products such as wood and wood-related materials such as sawdust, waste paper; sugar processing residues such as bagasse and beet pulp, or mixtures thereof.

Alternatively, a biomass material may be treated under high temperature at a short contact time to form a fast pyrolysis oil that can then undergo a fluid catalytic cracking process, such as the processes described in U.S. Pat. No. 9,120,989. Suitable biomass materials include wood, wood residues, sawdust, slash bark, thinnings, forest cullings, begasse, corn fiber, corn stover, empty fruit bunches (EFB), fronds, palm fronds, flax, straw, low-ash straw, energy crops, palm oil, non-food-based biomass materials, crop residue, slash, pre-commercial thinnings and tree residue, annual covercrops, switchgrass, miscanthus, cellulosic containing components, cellulosic components of separated yard waste, cellulosic components of separated food waste, cellulosic components of separated municipal solid waste (MSW), or combinations thereof.

Polymerization Processes

Polymerization processes of the present disclosure include the polymerization of $C_2$-$C_{30}$ alpha-olefins. $C_4$-$C_{30}$ internal olefins, branched $C_5$-$C_{30}$ internal olefins, or a mixture thereof, to provide at least one $C_6$-$C_{100}$ polyolefin product. A process involves contacting a feed including one or more $C_2$-$C_{30}$ alpha-olefin, one or more $C_4$-$C_{30}$ internal olefin, one or more of branched $C_5$-$C_{30}$ internal olefins or a mixture thereof, with at least one catalyst compound comprising a group 8, 9, 10, or 11 transition metal and at least one heteroatom.

Polymerization processes may occur in one or more polymerization reactors, in series or in parallel, at a reactor pressure of from 0 psig to 1000 psig; and a reactor temperature of about 250° C. or less.

The $C_2$-$C_{30}$ alpha-olefins, the linear $C_4$-$C_{30}$ internal olefins, the branched $C_5$-$C_{30}$ internal olefins, or a mixture thereof, can be introduced to a polymerization reactor in a liquid state, and or in a gaseous state, or in a partially liquid-partially gaseous state. When injected in the polymerization reactor in a liquid state, and or in a gaseous state, or in a partially liquid-partially gaseous state, the linear $C_4$-$C_{30}$ internal olefins, the branched $C_5$-$C_{30}$ internal olefins, or a mixture thereof, can be vaporized upon entry, such as the $C_2$-$C_{30}$ alpha-olefins, the linear $C_4$-$C_{30}$ internal olefins, the branched $C_5$-$C_{30}$ internal olefins, or a mixture thereof can be contacted in the gaseous state with the catalyst compound(s) of the present disclosure.

In at least one embodiment, the polymerization process includes contacting the $C_2$-$C_{30}$ alpha-olefins, the linear $C_4$-$C_{30}$ internal olefins, the branched $C_5$-$C_{30}$ internal olefins, or a mixture thereof, neat or in the presence of a solvent, with a catalyst or catalyst system; at a temperature of from about 250° C. or less, such as from about −35° C. to about 120° C., such as from about (0° C. to about 80° C., such as from about 10° C. to about 50° C., such as from about 15° C. to about 40° C., such as room temperature; and or at a pressure of from about 0 psig to about 1000 psig such as from about 0 psig to about 200 psig, such as from about 0 psig to about 100 psig.

For example, the polymerization process may include contacting one or more $C_5$ olefins (e.g., $C_5$ alpha-olefin, linear $C_5$ internal olefins, branched $C_5$ internal olefin, or a mixture thereof); neat or in the presence of a solvent, with a catalyst or catalyst system; at a temperature of from about 250° C. or less, such as from about −35° C. to about 120° C., such as from about 0° C. to about 80° C., such as from about 10° C. to about 50° C., such as from about 15° C. to about 40° C. such as room temperature; and or at a pressure of from about 0 psig to about 1000 psig such as from about 0 psig to about 200 psig, such as from about 0 psig to about 100 psig.

The one or more $C_5$ olefins can be independently selected from 2-Me-2-butene, 2-Me-1-butene, 3-Me-1-butene, 1-pentene, cis-2-pentene, trans-2-pentene, or mixture thereof.

A catalyst system may include one or more of: i) at least one catalyst compound comprising a group 8, 9, 10, or 11 transition metal and at least one heteroatom; ii) an activator; iii) and optionally a support. The catalyst compound and activator may be combined in any order, and can be combined prior to contacting with the $C_2$-$C_{30}$ alpha-olefins, the linear $C_4$-$C_{30}$ internal olefins, the branched $C_5$-$C_{30}$ internal olefins, or a mixture thereof. The $C_6$-$C_{100}$ polyolefin products of the present disclosure can be linear $C_6$-$C_{100}$ polyolefin products, such as linear $C_{10}$-$C_{25}$ polyolefin products.

In a polymerization process, a feed stream comprising the $C_2$-$C_{30}$ alpha-olefins, the $C_4$-$C_{30}$ internal olefins, and branched olefin or a mixture thereof, such as a feed stream comprising from about 0 wt % to about 20 wt % of $C_2$-$C_{30}$ alpha-olefins, from about 10 wt % to about 50 wt % of linear $C_4$-$C_{30}$ internal olefins, from about 10 wt % to about 80 wt % of branched $C_5$-$C_{30}$ internal olefins, or a mixture thereof, is contacted with a catalyst compound described above, neat or in the presence of a solvent. The catalyst compound(s) may be activated by any suitable activator, such as an alkyl aluminoxane, but an activator is not needed. In at least one embodiment, an alkyl aluminoxane is an alkyl aluminoxane of triethylethoxyaluminium, methyl aluminoxane (MAO) or modified methyl aluminoxane (MMAO). The solvent may be a saturated hydrocarbon or an aromatic solvent such as n-pentane, isopentanes, n-hexane, n-heptane, cyclohexane, benzene, toluene, xylenes, or a mixture thereof. Furthermore, the solvent can be a mixture of one or more alkanes with one or more olefin, such as the volume ratio alkane/olefin can be 1:1, such as 0.5:1, such as 0:1. For example, one or more $C_5$ alkanes can be used as a solvent to mix with one or more olefins, at a volume ratio of $C_5$ alkanes/$C_5$ olefins of 100:1 to 1:100

The polymerization process may include contacting the $C_2$-$C_{30}$ alpha-olefins, the linear $C_4$-$C_{30}$ internal olefins, the branched $C_5$-$C_{30}$ internal olefins, or a mixture thereof, with the catalyst compound including a group 8, 9, 10, or 11 transition metal and at least one heteroatom, neat or in the presence of a solvent, at a weight ratio of olefin to solvent of from about 1:0.001 to about 1:10, such as from about 1:0 to about 1:1, such as from about 90:10 to about 60:40, such as from about 80:20 to about 70:30 to about 100:1.

The polymerization process may include contacting the $C_2$-$C_{30}$ alpha-olefins, the linear $C_4$-$C_{30}$ internal olefins, the branched $C_5$-$C_{30}$ branched olefins, or a mixture thereof with the catalyst system comprising one or more of: i) at least one catalyst compound including a group 8, 9, 10, or 11 transition metal and at least one heteroatom (e.g., fluorine); ii) an optional activator; iii) and optionally a support; neat or in the presence of a solvent; at a weight ratio of olefin to solvent of from about 1:0 to about 1:10, such as from about 1:0 to about 1:1, such as from about 90:10 to about 60:40, such as from about 80:20 to about 70:30.

Contacting the catalyst compound with a feedstream comprising the $C_2$-$C_{30}$ alpha-olefins, the linear $C_4$-$C_{30}$ internal olefins, the branched $C_5$-$C_{30}$ internal olefins, or a mixture thereof, may be carried out in an atmosphere inert under the process conductions, such as in nitrogen, argon, or a mixture thereof.

When an activator is employed, a molar ratio of group 8, 9, 10, or 11 transition metal catalyst to activator (e.g., alkyl aluminoxane) (representative of alkyl aluminoxane to group 8, 9, 10, or 11 transition metal catalyst) can be from about 10:1 to about 1:1,000, such as from about 1:1 to about 1:700, such as from about 1:500 to about 1:200, such as from about 10:1 to about 1:5. For example, a molar ratio of Ni catalyst to activator (e.g., alkyl aluminoxane) (representative of alkyl aluminoxane to Ni catalyst) can be from about 10:1 to about 1:1.000, such as from about 1:1 to about 1:700, such as from about 1:500 to about 1:200, such as from about 10:1 to about 1:5. In at least one embodiment, the molar ratio of catalyst compound to activator is from about 10:1 to about 1:5, such as from about 5:1 to about 1:4, such as from about 1:3.

A catalyst loading % (based on the concentration of monomer) can be from about 0.0001 mol % to about 5 mol %, such as from about 0.001 mol % to about 2.5 mol %, such as from about 0.01 mol % to about 1 mol %, such as from about 0.1 mol % to about 0.75 mol %, such as about 0.2 mol %, for example.

In at least one embodiment, the TON of the catalyst compound is about 10 or greater, such as from about 10 to about 1,000,000, such as from about 15 to about 10,000, such as from about 20 to about 1,000.

In at least one embodiment, a polymerization of $C_2$-$C_{30}$ alpha-olefin(s), linear $C_4$-$C_{30}$ internal olefin(s), branched $C_5$-$C_{30}$ internal olefin(s), or a mixture thereof, is performed at a temperature of from about 120° C. or less, such as from about −35° C. to about 120° C., such as from about −30° C. to about 100° C., such as from about −25° C. to about 80° C., such as from about 0° C. to about 70° C., such as room temperature, for example. A polymerization of the present disclosure may be carried out by mixing a solution of internal olefin and the catalyst(s), cooling the solution, adding activator to the cooled solution, and optionally allowing the mixture to increase in temperature. A polymerization can be performed at ambient pressure for a period of time, such as from about 1 minute to about 240 hours, such as from about 5 minutes to about 48 hours, such as from about 30 minutes to about 24 hours, alternatively from about 4 hours to about 48 hours, alternatively from about 1 minute to about 1 hour, such as about 1 minute to about 30 minutes, such as about 5 minutes to about 15 minutes.

In at least one embodiment, $C_2$-$C_{30}$ alpha-olefins and or $C_4$-$C_{30}$ internal olefins are converted to $C_6$-$C_{100}$ polyolefin product(s) at a conversion (%) of from about 10% to about 99%, such as from about 20% to about 80%, such as from about 30% to about 70%, such as from about 40% to about 80%, such as from about 50% to about 60%.

A polymerization can be terminated, for example, by addition of an acid solution, such as 3% HCl-MeOH, which decomposes the catalyst mixture. The polyolefin products obtained can be washed with a solvent, such as water, and separated by liquid-liquid separation or distillation.

Polymerization Catalysts

Polymerization catalyst compounds of the present disclosure may include one or more group 8, 9, 10, or 11 transition metal and at least one heteroatom. In at least one embodiment, the group 8, 9, 10 or 11 transition metal is nickel, palladium, cobalt, or iron, such as the catalyst compound includes nickel. It has been discovered that polymerization of internal olefins (linear and branched), as well as alpha olefins occurs when the catalyst compound is a nickel catalyst, which may include one or more fluorine atoms. Furthermore, it has been discovered that catalyst compounds of the present disclosure, for example catalyst compounds that include at least one fluorine atom, can polymerize branched internal olefins. Additionally, polymerization catalysts of the present disclosure also provide low molecular weight polymers (e.g., ≤1,000 g/mol).

In at least one embodiment, a catalyst compound, and catalyst systems including such compounds, is represented by Formula (I):

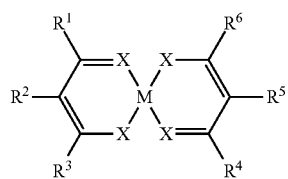

(I)

wherein:
M is a group 8, 9, 10, or 11 metal;
X is an heteroatom; and
each of $R^1$, $R^2$, $R^3$, $R^4$, $R^5$, and $R^6$ is independently selected from hydrogen, $C_1$-$C_{40}$ hydrocarbyl, $C_1$-$C_{40}$ substituted hydrocarbyl, a heteroatom or a heteroatom-containing group, wherein at least one of $R^1$, $R^2$, $R^3$, $R^4$, $R^5$, and $R^6$ is a heteroatom or a heteroatom-containing group, or one or more of $R^1$ and $R^2$, $R^2$ and $R^3$, $R^4$ and $R^5$, or $R^7$ and $R^6$ are joined to form one or more substituted hydrocarbyl rings, unsubstituted hydrocarbyl rings, substituted heterocyclic rings, or unsubstituted to heterocyclic rings each having 5, 6, 7, or 8 ring atoms, wherein at least one of the rings is substituted with a heteroatom or a heteroatom-containing group if the remainder of R groups of Formula (I) are not a heteroatom or a heteroatom-containing group.

At least one of $R^1$, $R^2$, $R^3$, $R^4$, $R^5$, and $R^6$ are independently selected from a halogen or a halogen-containing group. For example, $R^1$ can be a halogen or a halogen-containing group, and each $R^2$, $R^3$, $R^4$, $R^5$, or $R^6$ groups can be independently selected from hydrogen, $C_1$-$C_{10}$ substituted alkyl, $C_1$-$C_{10}$ unsubstituted alkyl, $C_1$-$C_{10}$ substituted aryl, $C_1$-$C_{10}$ unsubstituted aryl, such as each of $R^2$, $R^3$, $R^4$, $R^5$, and $R^6$ can be independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may be halogenated, substituted hydrocarbyl radicals or an isomer of substituted hydrocarbyl radicals including trimethylsilylpropyl, trimethylsilylmethyl, trimethylsilylethyl, phenyl, or an isomer of hydrocarbyl substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, or dipropylmethylphenyl. In at least one embodiment, $R^1$ is a halogen or a halogen-containing group, and each of $R^2$, $R^3$, $R^4$, $R^5$, and $R^6$ is independently selected from hydrogen, unsubstituted phenyl, substituted phenyl, unsubstituted carbazole, substituted carbazole, unsubstituted naphthyl, substituted naphthyl, unsubstituted anthracenyl, substituted anthracenyl, unsubstituted fluorenyl, or substituted fluorenyl, a heteroatom or a heteroatom-containing group. In at least one embodiment, each of $R^1$, $R^3$, $R^4$, or $R^6$ is $CF_3$, and each of $R^2$ and $R^5$ is independently selected from hydrogen, methyl, isopropyl, or fluorine.

Furthermore, M can be Ni, Pd, Co, Cu, Rh, or Fe, such as M can be Ni. Each X can be independently selected from O, S, P and N.

It has further been discovered that a catalyst system including a nickel catalyst comprising fluorine also provides novel polyolefin products that provide, for example, a high cetane number after hydrogenation which are suitable as diesel fuels.

Catalyst compounds of the present disclosure, such as nickel catalysts described above, are advantageous internal olefin polymerization catalysts as they are typically not inhibited during a polymerization process by the presence of an aromatic solvent. Nickel catalysts of the present disclosure can also polymerize alpha-olefin feeds, and or alpha-olefin feed present in an internal olefin feed (such as a linear alpha-olefin or an internal olefin that also has terminal unsaturation). In comparison, early transition metal catalysts used to polymerize olefins are only compatible with alpha-olefins and are often incompatible in the presence of internal olefins. In addition, acid catalyzed polymerization produces branched products that do not have high cetane numbers after hydrogenation.

Catalyst compounds of the present disclosure, such as a Ni catalyst comprising at least one heteroatom can be prepared according to any suitable method, for example as reported in D. L. Beach, J. E. Bozik, C. Y. Wu, Y. V. Kissin, J. Mol. Catal. 1986, 34, pp 345-354, which is incorporated by reference herein, or can be obtained from commercial sources (e.g., Ni(hfacac)$_2$ available from Sigma-Aldrich).

In at least one embodiment, one or more different catalyst compound(s) are present in a catalyst system including an activator, and an optional support material. One or more different catalyst compound(s) can be present in the reaction zone where the process(es) described herein occur. When at least two catalyst compounds are used in one reactor as a mixed catalyst system, the two catalyst compounds can be chosen such that the two are compatible. A simple screening method, such as by $^1$H-NMR or $^{13}$C-NMR, can be used to determine which catalyst compounds are compatible.

The two catalyst compounds (pre-catalysts) may be used in any ratio. Molar ratios of (A) catalyst compound to (B) catalyst compound can be a range of (A:B) of from 1:1000 to 1000:1, alternatively 1:100 to 500:1, alternatively 1:10 to 200:1, alternatively 1:1 to 100:1, alternatively 1:1 to 75:1, and alternatively 5:1 to 50:1. The particular ratio chosen will depend on the exact pre-catalysts chosen, the process of activation, and the end product desired. In at least one embodiment, when using the two pre-catalysts, where both are activated with the same activator, mole percentages, based upon the molecular weight of the pre-catalysts, can be from 10% to 99.9% A to 0.1% to 90% B, alternatively 25% to 99% A to 0.5% to 75% B, alternatively 50% to 99% A to 1% to 50% B, and alternatively 75% to 99% A to 1% to 10% B.

Activators

The terms "cocatalyst" and "activator" are used herein interchangeably and are defined to be a compound which can activate a catalyst compound of the present disclosure by converting the neutral catalyst compound to a catalytically active catalyst compound cation.

After the catalyst compounds described above have been synthesized, catalyst systems may be formed by combining them with activators in any suitable manner including by supporting them for use in a polymerization. The catalyst systems may also be added to or generated in solution polymerization or bulk polymerization (in the monomer). Suitable catalyst systems may include a catalyst compound as described above and an activator such as aluminoxane.

Non-limiting activators, for example, include aluminoxanes, aluminum alkyls, ionizing activators, which may be neutral or ionic, and conventional-type cocatalysts. Activators can include aluminoxane compounds, modified aluminoxane compounds, and ionizing anion precursor compounds that abstract a reactive, σ-bound, metal ligand making the catalyst compound cationic and providing a charge-balancing non-coordinating or weakly coordinating anion.

Aluminoxane Activators

In at least one embodiment, aluminoxane activators are utilized as an activator in the catalyst system. Aluminoxanes are generally oligomeric compounds containing —Al(R')—O— sub-units, where R' is an alkyl group. Examples of aluminoxanes include methylaluminoxane (MAO), modified methylaluminoxane (MMAO), ethylaluminoxane and isobutylaluminoxane. As used herein, "MMAO" is a modified methyl aluminoxane which contains some higher alkyl groups which can improve solubility in non-polar solvents. A useful MMAO is MMAO cocatalyst type 3A (commercially available from Akzo Chemicals, Inc. under the trade name Modified Methylaluminoxane type 3A, described in U.S. Pat. No. 5,041,584).

Alkylaluminoxanes and modified alkylaluminoxanes are suitable as catalyst activators, particularly when the abstractable ligand is an alkyl, halide, alkoxide or amide. Mixtures of different aluminoxanes and modified aluminoxanes may also be used. It may be suitable to use a visually clear methylaluminoxane. A cloudy or gelled aluminoxane can be filtered to produce a clear solution or clear aluminoxane can be decanted from the cloudy solution. Another suitable aluminoxane is solid polymethylaluminoxane as described in U.S. Pat. Nos. 9,340,630; 8,404,880; and 8,975,209. Aluminum alkyls are available as hydrocarbon solutions from commercial sources. Methylaluminoxane ("MAO") is available from Albemarle as a 30 wt % solution in toluene.

When the activator is an aluminoxane (modified or unmodified), the activator to catalyst compound molar ratio can be a 1:1 molar ratio. An activator to catalyst compound molar ratio may be from 1:1 to 500:1, such as from 1:1 to 200:1, such as from 1:1 to 100:1, such as from 1:1 to 50:1.

In an alternate embodiment, little or no aluminoxane is used in the polymerization processes described herein. For example, aluminoxane can be present at zero mole %, alternately the aluminoxane can be present at a molar ratio of aluminum to catalyst compound transition metal less than 500:1, such as less than 300:1, such as less than 100:1, such as less than 1:1. In at least one embodiment, the aluminoxane is present at a molar ratio of aluminum to catalyst compound transition metal of 100:1 or more.

In at least one embodiment, aluminoxane is present at a molar ratio of aluminum to catalyst compound transition metal of from about 10:1 to about 1:5, such as from about 1:3, for example.

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may include an inert support material. The supported material can be a porous support material, for example, talc, and inorganic oxides. Other support materials include zeolites clays, organoclays, MOFs (e.g., MOF-5 ($Zn_4O(BDC)_3$, MOF-74, MOF-253, UiO-66-$NH_2$, NU-1000) or any other suitable organic or inorganic support material, or mixtures thereof.

The support material can be an inorganic oxide in a finely divided form. Suitable inorganic oxide materials for use in catalyst systems herein include groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. In at least one embodiment, the support material is selected from $Al_2O_3$, $ZrO_2$, $SiO_2$, $SiO_2/Al_2O_3$, $SiO_2/TiO_2$, silica clay, silicon oxide/clay, or mixtures thereof.

The support material, such as an inorganic oxide, can have a surface area in the range of from about 10 $m^2$/g to about 700 $m^2$/g, pore volume in the range of from about 0.1 $cm^3$/g to about 4.0 $cm^3$/g and average particle size in the range of from about 5 μm to about 500 μm. The surface area of the support material can be in the range of from about 50 $m^2$/g to about 500 $m^2$/g, pore volume of from about 0.5 $cm^3$/g to about 3.5 $cm^3$/g and average particle size of from about 10 μm to about 200 μm. For example, the surface area of the support material is in the range is from about 100 $m^2$/g to about 400 $m^2$/g, pore volume from about 0.8 $cm^3$/g to about 3.0 $cm^3$/g and average particle size is from about 5 μm to about 100 μm. The average pore size of the support material useful in the present disclosure is in the range of from 10 Å to 1000 Å, such as 50 Å to about 500 Å, and such as 75 Å to about 350 Å. In at least one embodiment, the support material is a high surface area, amorphous silica (surface area=300 $m^2$/gm; pore volume of 1.65 $cm^3$/gm). Silicas can be marketed under the tradenames of DAVISON 952 or DAVISON 955 by the Davison Chemical Division of W.R. Grace and Company. In other embodiments DAVISON 948 is used. Alternatively, a silica can be ES-70™ silica (PQ Corporation, Malvern, Pa.) that has been calcined at 875° C.

The support material should be dry, that is, free of absorbed water. Drying of the support material can be effected by heating or calcining at about 100° C. to about 1000° C., such as at least about 600° C. When the support material is silica, it is heated to at least 200° C., such as about 200° C. to about 850° C., and such as at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of the present disclosure. The calcined support material is then contacted with at least one polymerization catalyst comprising at least one catalyst compound and an activator.

The support material, having reactive surface groups, such as hydroxyl groups, is slurried in a non-polar solvent and the resulting slurry is contacted with a solution of a catalyst compound and an activator. In at least one embodiment, the slurry of the support material is first contacted with the activator for a period of time in the range of from about 0.5 h to about 24 h, from about 2 h to about 16 h, or from about 4 h to about 8 h. The solution of the catalyst compound is then contacted with the isolated support/activator. In at least one embodiment, the supported catalyst system is generated in situ. In alternate embodiment, the slurry of the support material is first contacted with the catalyst compound for a period of time in the range of from about 0.5 h to about 24 h, from about 2 h to about 16 h, or from about 4 h to about 8 h. The slurry of the supported catalyst compound is then contacted with the activator solution.

The mixture of the catalyst compound, optional activator and optional support is heated to about 0° C. to about 250° C., such as about 0° C. to about 70° C., such as about 23° C. to about 60° C., such as at room temperature. Contact times may range from about 0.5 h to about 24 h, from about 2 h to about 16 h, or from about 4 h to about 8 h.

Suitable non-polar solvents are materials in which all of the reactants used herein, e.g., the activator and the catalyst compound, are at least partially soluble and which are liquid at reaction temperatures. Non-polar solvents can be alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polyolefin Products

The present disclosure relates to compositions of matter produced by the processes described herein. Processes of the present disclosure provide novel compositions comprising one or more $C_6$-$C_{100}$ polyolefin products, such as $C_8$-$C_{50}$ polyolefin products, such as $C_{10}$-$C_{40}$ polyolefin products, such as $C_{10}$-$C_{25}$ polyolefin products. Alternatively, polyolefin products produced in accordance with processes of the present disclosure can be diesel fuels that have a high cetane number (e.g., after hydrogenation).

A polyolefin product of the present disclosure can be a $C_6$-$C_{100}$ polyolefin product, such as a $C_8$-$C_{50}$ polyolefin product, such as a $C_{10}$-$C_{40}$ polyolefin product, such as a $C_{12}$-$C_{25}$ polyolefin product.

A polyolefin product can have less than 3 $sp^2$ hybridized carbons (e.g., substantially all (e.g., >99 wt %) of the polyolefin compounds of the polyolefin product have less than 3 $sp^2$ hybridized carbons), such as a polyolefin product having 2 $sp^2$ hybridized carbons. A polyolefin product of the present disclosure has one olefin (e.g., substantially all (e.g., >99 wt %) of the polyolefin compounds of the polyolefin product have one olefin). Furthermore, the polyolefin product of the present disclosure can have a carbon number of "Cn", where n is from about 6 to about 100, such as from about 10 to about 80, such as from about 10 to about 25, alternatively from about 25 to about 50. Furthermore, the polyolefin product of the present disclosure can have a number of monomers "X" in the polyolefin polymer product, where X can be from 2 to 25, such as from about 5 to about 20, such as from about 10 to about 15.

The starting olefin monomer may have a number of branches (referred to as "B"). For example, 1-pentene is linear with B equal to 0 and 2-methyl-2-butene has one branch with B is equal to 1. The polyolefin product may have a number of branches depending on B of the starting olefin and X, the number of monomer unit. For example, a dimer product (X=2) from 1-pentene (B=0) can have number of branches ranging from (B)(X)=0 to (B+1)X−1=1. The dimer product (X=2) of 2-methyl-2-butene (B=1) will have number of branches ranging from (B)(X)=2 to (B+1)X−1=3. In a further example, the polyolefin product can have from (B)X to (B+1)X−1 branches, where B can be from 0 to 4, such as from 0 to 3 such as from about 1 to about 2; X can be from 2 to 25, such as from about 5 to about 20, such as from about 10 to about 15.

The branching structures of the polyolefin products can be determined by $^{13}C$ NMR spectroscopy (which can include Distortionless Enhancement by Polarization Transfer at 135 degree pulse flip angle, known as "DEPT135" spectroscopy). $^{13}C$ NMR spectroscopy differentiates the types of carbon in the polyolefin product sample (e.g., $CH_3$, $CH_2$, CH, and quaternary C). For a mixture of polyolefin products, the mixture can be first separated by gas chromatography and then its individual components can be identified by mass spectrometry. The overall branching structures can be determined by $^{13}C$ NMR The various types of carbon atoms of a polyolefin product of the present disclosure can be determined using $^1H$ and $^{13}C$ NMR spectroscopy.

The $C_6$-$C_{100}$ polyolefin products may have a methylene content of from about 1 wt % to about 98 wt %, such as from about 5 wt % to about 85 wt %, such as from about 10 wt % to about 75 wt %, based on the total weight of the $C_6$-$C_{100}$ polyolefin product.

The $C_6$-$C_{100}$ polyolefin products may have a methyl content of from about 1 wt % to about 75 wt %, such as from about 5 wt % to about 60 wt %, such as from about 10 wt % to about 50 wt %, based on the total weight of the $C_6$-$C_{100}$ polyolefin product.

The high amounts of di-substituted olefins and or alpha-olefins are more reactive than tri-substituted olefins which provide improved subsequent reactivity of the polyolefin products, such as faster hydrogenation processes (hydrogenation processes will be described further).

Compositions of the present disclosure formed after polymerization of, for example, one or more $C_5$ olefins, such as compositions formed after polymerization of 2-Me-2-butene, 2-Me-1-butene, 3-Me-1-butene, 1-pentene, 2-pentene, or a mixture thereof, can be further catalytically hydrogenated to form a $C_6$-$C_{100}$ hydrogenated polyolefin product, such as a substituted or unsubstituted polymer product. A $C_6$-$C_{100}$ hydrogenated polyolefin product can be used as diesel fuel. Also, a $C_6$-$C_{100}$ hydrogenated polyolefin product can be used as a lubricating oil base stock.

Base Stocks

In at least one embodiment, a base stock is a $C_6$-$C_{100}$ polyolefin product, such as a $C_{25}$-$C_{50}$ polyolefin product.

A polyolefin product of the present disclosure, when added to an oil (as a viscosity modifier) or used as an oil, can reduce the tendency of the oil to change its viscosity with temperature in order to improve its viscosity index (VI) and flow characteristics. Improving VI helps in maintaining constant the flow properties of the protective oil film. This means a high enough viscosity to avoid damage on engine parts when the temperature rises because of the engine heat and a low enough viscosity against the cold start and pumping. Polyolefin products of the present disclosure can have a VI of about 100 or greater, about 120 or greater, such as about 140 or greater, such as about 150 or greater, such as about 170 or greater, such as about 180 or greater, as determined according to ASTM D2270.

In addition, base stocks are affected by many properties including kinematic viscosity (KV), where an inverse relationship exists between KV and low-temperature fluidity, and VI, where a direct relationship exists between VI and low-temperature fluidity. Increasing the VI of a base stock by adding a polymer product of the present disclosure can provide improved viscometrics under both low-temperature and high-temperature regimes. VI itself represents the change in viscosity over a temperature range from 40° C. to 100° C. The higher the VI, the lower the oil's viscometric properties will change, and the flatter its profile will be over the temperature range. This can be extended to higher and lower temperatures. In at least one embodiment, a polyolefin product of the present disclosure can have a kinematic viscosity at 100° C. (KV100), as determined by ASTM D445, of about 2 cSt to about 25 cSt, such as from about 3 cSt to about 18 cSt, such as from about 4 cSt to about 10 cSt. Additionally or alternatively, a polyolefin product of the present disclosure can have a kinematic viscosity at 40° C. (KV40), as determined by ASTM D445, of about 7 cSt to about 240 cSt, such as from about 12 cSt to about 155 cSt, such as from about 18 cSt to about 70 cSt.

In addition, glass transition temperature (Tg) is indicative of the fluidity of a material at low temperature operations. Tg can be measured using Differential Scanning Calorimetry (DSC) on a commercially available instrument (e.g., TA Instruments 2920 DSC). Tg is measured by sequilibrating the sample at 100° C., isothermal for 5 min, ramping the temperature at 10° C./min to −100° C., isothermal for 5 min, ramping the temperature at 10° C./min to 100° C., and isothermal for 2 min.

Hydrogenation of Polyolefin Products and Production of Diesel Fuels, Lubricants, and Base Stocks A polyolefin product formed by a polymerization process can be catalytically hydrogenated to form a hydrogenated polyolefin product. A hydrogenated polyolefin product can be used as diesel fuel and or a lubricating oil base stock. The hydrogenation may be carried out in solution. The catalyst may be any suitable hydrogenation catalyst, such as a palladium catalyst supported on activated carbon or a Raney nickel catalyst. The hydrogenation can be carried out at elevated pressure, e.g., from 100 KPa to 10,000 KPa, such as from 100 KPa to 5,000 KPa. The hydrogenation reaction can be carried out at a temperature of from 15° C. to 200° C., such as from 30° C. to 70° C. The duration of the hydrogenation reaction may be from a few minutes to several days. After the hydrogenation reaction is complete, the reaction mixture can be cooled, depressurized and the solvent removed by vacuum distillation. The purity of the hydrogenated product can be determined by $^1$H NMR by detecting the disappearance of olefinic protons.

In at least one embodiment, a hydrogenation is performed using Ni/Kiselguhr as the catalyst, 1 mol % to 5 mol %, under 200 psi to 400 psi of hydrogen at a temperature of from about 150° C. to about 200° C. for about 4 hours.

Hydrogenated Polyolefin Product

In at least one embodiment, a hydrogenated diesel fuel and or a hydrogenated base stock is a $C_6$-$C_{100}$ hydrogenated polyolefin product, such as a $C_6$-$C_{50}$ hydrogenated polyolefin product, such as a $C_9$-$C_{25}$ hydrogenated polyolefin product. Low amounts of methyl (—$CH_3$) and methane (CH) can be indicative of high linearity of a hydrogenated polyolefin product.

A hydrogenated polyolefin product can have less than 3 $sp^2$ hybridized carbons, such as substantially free of (or free of) $sp^2$ hybridized carbons (e.g., substantially all (e.g., >99 wt %) of the hydrogenated polyolefin compounds of the hydrogenated polyolefin product are substantially free of (or free of) $sp^2$ hybridized carbons). A hydrogenated polyolefin product of the present disclosure can be substantially free of (or free of) olefin content (e.g., substantially all (e.g., >99 wt %) of the hydrogenated polyolefin compounds of the hydrogenated polyolefin product are substantially free of (or free of) olefin content). Furthermore, the hydrogenated polyolefin product of the present disclosure can have a carbon number of "Cn", where n is from about 6 to about 100, such as from about 10 to about 80, such as from about 10 to about 25, alternatively from about 25 to about 50. Furthermore, the hydrogenated polyolefin product of the present disclosure can have a number of monomers "X" in the polyolefin polymer product, where X can be from 2 to 25, such as from about 5 to about 20, such as from about 10 to about 15.

The polyolefin product may have a number of branches (referred to as "B"). For example, a hydrogenated polyolefin product is linear with B equal to 0. The polyolefin product may have a number of branches depending on B of the starting olefin and X, the number of monomer units that formed the polyolefin product. For example, a dimer product (X=2) from 1-pentene (B=0) can have number of branches ranging from (B)(X)=0 to (B+1)X−1=1. The dimer product (X=2) of 2-methyl-2-butene (B=1) can have number of branches ranging from (B)(X)=2 to (B+1)X−1=3. In a further example, the polyolefin product can have from (B)(X) to (B+1)X−1 branches, where B can be from 0 to 4, such as from 0 to 3 such as from about 1 to about 2; X can be from 2 to 25, such as from about 5 to about 20, such as from about 10 to about 15.

Process of the present disclosure provide novel compositions comprising one or more $C_6$-$C_{100}$ hydrogenated polyolefin products, such as $C_5$-$C_{50}$ hydrogenated polyolefin products, such as $C_{10}$-$C_{40}$ hydrogenated polyolefin products, such as $C_{12}$-$C_{25}$ hydrogenated polyolefin products. Hence, compositions including one or more $C_6$-$C_{100}$ polyolefin products can be catalytically hydrogenated to form compositions including one or more $C_6$-$C_{100}$ hydrogenated polyolefin product, such as $C_6$-$C_{100}$ substituted or $C_6$-$C_{100}$ unsubstituted polymer products.

For example, compositions including polyolefin products formed after polymerization (for example, polymerization of one or more $C_5$ olefins (e.g., 2-Me-2-butene, 2-Me-1-butene, 3-Me-1-butene, 1-pentene, 2-pentene, or mixture thereof)), can be further hydrogenated under the conditions described above, forming novel hydrogenated polyolefin products. For example, a hydrogenated polyolefin product may have one or more of:

(1) a 2,3,6-trimethylheptane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 15 wt %, based on the total weight of the hydrogenated polyolefin products;

(2) a 2,3,5-trimethylheptane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(3) a 2,5-dimethyloctane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(4) a 2,7-dimethyloctane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(5) a 5-ethyl-2-methylheptane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(6) a 2,6-dimethyloctane content of from about 0.1 wt % to about 100 wt %, such as from about 0.1 wt % to about 75 wt %, such as from about 0.1 wt % to about 50 wt %, such as from about 0.1 wt % to about 40 wt %, such as from about 0.1 wt % to about 30 wt %, such as from about 0.1 wt % to about 20 wt %, such as from about 0.1 wt % to about 15 wt %, based on the total weight of the hydrogenated polyolefin products;

(7) a 3,6-dimethyloctane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(8) a 2,3-dimethyloctane content of from about 0.1 wt % to about 100 wt %, such as from about 0.1 wt % to about 75 wt %, such as from about 0.1 wt % to about 50 wt %, such as from about 0.1 w, % to about 25 wt %, such as from about 0.1 wt % to about 10 wt %, based on the total weight of the hydrogenated polyolefin products;

(9) a 4-Me-nonane content of from about 0.1 wt % to about 100 wt %, such as from about 0.1 wt % to about 75 wt %, such as from about 0.1 wt % to about 50 wt %, such as from about 0.1 wt % to about 40 wt %, such as from about 0.1 wt % to about 30 wt %, such as from about 0.1 wt % to about 20 wt %, based on the total weight of the hydrogenated polyolefin products;

(10) a 2-Me-nonane content of from about 0.1 wt % to about 100 wt %, such as from about 0.1 wt % to about 75 wt %, such as from about 0.1 wt % to about 50 wt %, such as from about 0.1 wt % to about 25 wt %, such as from about 0.1 wt % to about 10 wt %, such as from about 0.1 wt % to about 5 wt %, based on the total weight of the hydrogenated polyolefin products;

(11) a 3-Et-octane content of from about 0.1 wt % to about 100 wt %, such as from about 0.1 wt % to about 100 wt %, such as from about 0.1 wt % to about 75 wt %, such as from about 0.1 wt % to about 50 wt %, such as from about 0.1 wt % to about 40 wt %, such as from about 0.1 wt % to about 30 wt %, such as from about 0.1 wt % to about 20 wt %, based on the total weight of the hydrogenated polyolefin products;

(12) a 3-Me-nonane content of from about 0.1 wt % to about 100 wt %, such as from about 0.1 wt % to about 100 wt %, such as from about 0.1 wt % to about 75 wt %, such as from about 0.1 wt % to about 50 wt %, such as from about 0.1 wt % to about 40 wt %, such as from about 0.1 wt % to about 30 wt %, such as from about 0.1 wt % to about 20 wt %, such as from about 0.1 wt % to about 10 wt %, based on the total weight of the hydrogenated polyolefin products; and or

(13) a decane content of from 0.1 wt % to about 100 wt %, such as from about 0.1 wt % to about 100 wt %, such as from about 0.1 wt % to about 75 wt %, such as from about 0.1 wt % to about 50 wt %, such as from about 0.1 wt $ to about 40 wt %, such as from about 0.1 wt % to about 30 wt %, such as from about 0.1 wt % to about 20 wt %, such as from about 0.1 wt % to about 10 wt %, based on the total weight of the hydrogenated polyolefin products %.

In at least one embodiment, a hydrogenated polyolefin product includes two or more of:
- a 2,3,6-trimethylheptane content of from about 0.1 wt % to about 12 wt %;
- a 2,3,5-trimethylheptane content of from about 0.1 wt % to about 1 wt %;
- a 2,5-dimethyloctane content of from about 0.1 wt % to about 5 wt %;
- a 2,7-dimethyloctane content of from about 0.1 wt % to about 5 wt %;
- a 5-ethyl-2-methylheptane content of from 0.1 wt % to about 5 wt %,
- a 2,6-dimethyloctane content of from 0.1 wt % to about 15 wt %;
- a 3,6-dimethyloctane content of from about 0.1 wt % to about 5 wt %;
- a 2,3-dimethyloctane content of from about 0.1 wt % to about 10 wt %;
- a 4-Me-nonane content of from about 0.1 wt % to about 20 wt %;
- a 2-Me-nonane content of from about 0.1 wt % to about 3 wt %;
- a 3-Et-octane content of from about 0.1 wt % to about 16 wt %;
- a 3-Me-nonane content of from about 0.1 wt % to about 10 wt %; and
- a decane content of from about 0.1 wt % to about 10 wt %, based on the total weight of the hydrogenated polyolefin products %.

A hydrogenated polyolefin product can have a methylene content of from about 1 wt % to about 98 wt %, such as from about 5 wt % to about 60 wt %, such as from about 10 wt % to about 30 wt %, such as from about 15 wt % to about 20 wt %, based on the total weight of the $C_6$-$C_{100}$ hydrogenated polyolefin product, as determined by GC measurements.

A hydrogenated polyolefin product can have a methyl content of from about 1 wt % to about 75 wt %, such as from about 5 wt % to about 50 wt %, such as from about 10 wt % to about 25 wt %, such as from about 15 wt % to about 20 wt %, based on the total weight of the $C_6$-$C_{100}$ hydrogenated polyolefin product, as determined by GC measurements.

Hydrogenated polyolefin products, as diesel fuels, base stocks, and or chemical intermediates, produced in accordance with processes of the present disclosure can possess high linearity which can provide improved flow, low temperature properties, and thickening efficiency. Alternatively, some hydrogenated polyolefin products can be used as diesel fuels having a high cetane number.

Lubricating Oils

Polyolefin products or hydrogenated polyolefin products of the present disclosure can be used as base stocks useful in engine oils. The polyolefin products and or hydrogenated polyolefin products can be in the lube oil boiling range, typically from about 100° C. to about 450° C.

The viscosity-temperature relationship of a lubricating oil is an aspect often considered when selecting a lubricant for a particular application. Viscosity index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translated into thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270. A lubricating oil of the present disclosure can have a VI of about 100 or greater, about 120 or greater, such as about 140 or greater, such as about 150 or greater, such as about 170 or greater, such as about 180 or greater, as determined according to ASTM D2270.

VI is related to kinematic viscosities measured at 40° C. and 100° C. using ASTM method D445. A lubricating oil of the present disclosure can have a kinematic viscosity at 100° C. (KV100), as determined by ASTM D445, of about 2 cSt to about 25 cSt, such as from about 3 cSt to about 18 cSt, such as from about 4 cSt to about 10 cSt. Additionally or alternatively, a lubricating oil of the present disclosure can have a kinematic viscosity at 40° C. (KV40), as determined by ASTM D445, of about 7 cSt to about 240 cSt, such as from about 12 cSt to about 155 cSt, such as from about 18 cSt to about 70 cSt.

Polyolefin products or hydrogenated polyolefin products of the present disclosure can be present in a lubricating oil in an amount of from about 1 wt % to about 99 wt %, such as from about 1 wt % to about 50 wt %, such as from about 1 wt % to about 25 wt %, such as from about 5 wt % to about 10 wt %, based on the weight of the lubricating oil.

Other Lubricating Oil Additives

A lubricating oil of the present disclosure may additionally contain one or more lubricating oil performance additives including but not limited to dispersants, other detergents, corrosion inhibitors, rust inhibitors, metal deactivators, other anti-wear agents and or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are from about 10,000 to about 1,000,000, such as about 20,000 to about 500,000, such as about 50,000 to about 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers having a molecular weight of from about 50,000 to about 200,000.

The amount of viscosity modifier in a lubricating oil of the present disclosure may range from zero to about 8 wt %, such as about 0.1 wt % to about 4 wt %, such as about 0.1 wt % to about 2 wt 0% based on the weight of the lubricating oil.

Antioxidants

Typical anti-oxidants include phenolic anti-oxidants, aminic anti-oxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such bi-phenol compounds linked by alkylene bridges sulfuric bridges or oxygen bridges. Alkyl phenols include mono- and poly-alkyl or alkenyl phenols, the alkyl or alkenyl group containing from 3 carbons to 100 carbons, such as 4 carbons to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

A phenolic anti-oxidant may be represented by the general formula

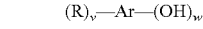

where Ar is selected from phenyl, naphthyl, biphenyl,

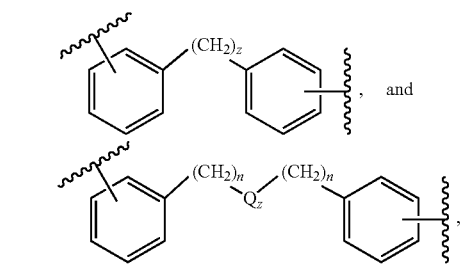

where R is a $C_3$-$C_{100}$ alkyl or alkenyl group, a sulfur substituted alkyl or alkenyl group, such as a $C_4$-$C_{50}$ alkyl or alkenyl group or sulfur substituted alkyl or alkenyl group, such as $C_3$-$C_{100}$ alkyl or sulfur substituted alkyl group, such as a $C_4$-$C_{50}$ alkyl group. Q is oxygen or sulfur. w is at least 1 to up to the available valences of Ar. v ranges from 0 to up to the available valances of Ar-w. z ranges from 1 to 10, n ranges from 0 to 20. In at least one embodiment, w ranges from 1 to 3, v ranges from 0 to 3, z ranges from 1 to 4 and n ranges from 0 to 5.

Phenolic anti-oxidant compounds can be the hindered phenolics and phenolic esters which contain a sterically hindered hydroxyl group, and these include those derivatives of dihydroxy aryl compounds in which the hydroxyl groups are in the o- or p-position to each other. Typical phenolic anti-oxidants include the hindered phenols substituted with $C_{1+}$ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4-alkoxy phenol; and

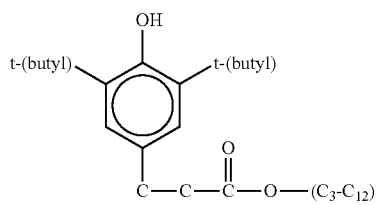

Phenolic type anti-oxidants in the lubricating industry include commercial examples such as Ethanox® 4710, Irganox® 1076, Irganox® L1035, Irganox® 1010, Irganox® L109, Irganox® L118, Irganox® L135 and the like.

The phenolic anti-oxidant can be present in a lubricating oil in an amount in the range of from 0.1 wt % to about 3 wt %, such as about 1 wt % to about 3 wt %, such as from about 1.5 wt % to about 3 wt % based on the weight of the lubricant oil.

Aromatic amine anti-oxidants include phenyl-α-naphthyl amine which is described by the following molecular structure:

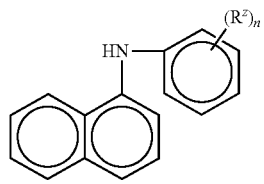

wherein $R^z$ is hydrogen or a $C_1$ to $C_{14}$ linear or $C_3$ to $C_{14}$ branched alkyl group, such as $C_1$ to $C_{10}$ linear or $C_3$ to $C_{10}$ branched alkyl group, such as linear or branched $C_6$ to $C_8$ and n is an integer ranging from 1 to 5, such as 1. A particular example is Irganox® L06.

Other aromatic amine anti-oxidants include other alkylated and non-alkylated aromatic amines such as aromatic monoamines of the formula $R^7R^8R^9N$ where $R^7$ is an aliphatic, aromatic or substituted aromatic group, $R^8$ is an aromatic or a substituted aromatic group, and $R^9$ is H, alkyl, aryl or $R^{10}S(O)_pR^{11}$ where $R^{10}$ is an alkylene, alkenylene, or aralkylene group, $R^{11}$ is a higher alkyl group, or an alkenyl, aryl, or alkaryl group, and p is 0, 1 or 2. The aliphatic group $R^7$ may contain from 1 carbon atom to 20 carbon atoms, or can contain from 6 carbon atoms to 12 carbon atoms. The aliphatic group is a saturated aliphatic group. For example, both $R^7$ and $R^8$ can be aromatic or substituted aromatic groups, and the aromatic group may be a fused ring aromatic group such as naphthyl. Aromatic groups $R^7$ and $R^8$ may be joined together with other groups such as S.

Typical aromatic amine anti-oxidants have alkyl substituent groups of at least 6 carbon atoms. Examples of aliphatic groups include hexyl, heptyl, octyl, nonyl, and decyl. Generally, the aliphatic groups will not contain more than 14 carbon atoms. The general types of such other additional amine anti-oxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of anti-oxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithio-phosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and or Cu(II) salts derived from alkenyl succinic acids or anhydrides are known to be particularly useful.

Such anti-oxidants may be used individually or as mixtures of one or more types of anti-oxidants, the total amount used in a lubricating oil being an amount of from about 0.50 wt % to about 5 wt %, such as about 0.75 wt % to about 3 wt %.

Detergents

Detergents may be included in lubricating oils of the present disclosure. In at least one embodiment, a detergent is an alkali or alkaline earth metal salicylate detergent.

A detergent can be alkali or alkaline earth metal phenates, sulfonates, carboxylates, phosphonates and mixtures thereof. The detergents can have total base number (TBN) ranging from neutral to highly overbased, e.g., TBN of 0 to 500 or greater, such as 2 to 400, such as 5 to 300, and they can be present either individually or in combination with each other in an amount in the range of from 0 wt % to about 10 wt %, such as about 0.5 wt % to about 5 wt % (active ingredient) based on the total weight of the formulated lubricating oil.

Other detergents can be calcium phenates, calcium sulfonates, magnesium phenates, magnesium sulfonates and other related components (including borated detergents).

Dispersants

During engine operation, oil-insoluble oxidation byproducts are produced. Dispersants help keep these byproducts in solution, thus diminishing their deposition on metal surfaces. Dispersants may be ashless or ash-forming. For example, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one nitrogen, oxygen, or phosphorus atom. Typical hydrocarbon chains contain from about 50 to about 400 carbon atoms.

In at least one embodiment, a dispersant is an alkenylsuccinic derivative, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Exemplary U.S. patents describing such dispersants are U.S. Pat. Nos. 3,172,892; 3,219,666; 3,316,177 and 4,234,435. Other types of dispersant are described in U.S. Pat. Nos. 3,036,003 and 5,705,458.

Hydrocarbyl-substituted succinic acid compounds may be used as dispersants. In particular, succinimide, succinate esters, or succinate ester amides prepared by the reaction of a hydrocarbon-substituted succinic acid compound, such as those having at least about 50 carbon atoms in the hydrocarbon substituent, with at least one equivalent of an alkylene amine.

Succinimides are formed by the condensation reaction between alkenyl succinic anhydrides and amines. Molar ratios can vary depending on the amine or polyamine. For example, the molar ratio of alkenyl succinic anhydride to TEPA can vary from 1:1 to 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range from about 800 to about 2,500. The above products can be post-reacted with various reagents such as sulfur, oxygen, formaldehyde, carboxylic acids such as oleic acid, and boron compounds such as borate esters or highly borated dispersants. The dispersants can be borated with from 0.1 to 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from about 800 to about 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average molecular weight of from about 600 to about 100,000.

Examples of $HN(R)_2$ group-containing reactants are alkylene polyamines, principally polyethylene polyamines. Other representative organic compounds containing at least one $HN(R)_2$ group suitable for use in the preparation of Mannich condensation products include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N$—$(Z$—$NH$—$)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines can be obtained by the reaction of ammonia and dihalo alkanes, such as dichloro alkanes. Thus the alkylene polyamines obtained from the reaction of 2 moles to 11 moles of ammonia with 1 mole to 10 moles of dichloroalkanes having 2 carbon atoms to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a form aldehyde-yielding reactant is exemplary.

Dispersants can include borated and non-borated succinimides, including those derivatives from mono-succinimides, bis-succinimides, and or mixtures of mono- and bis-succinimides, wherein the hydrocarbyl succinimide is derived from a hydrocarbylene group such as polyisobutylene having a molecular weight of from about 500 g/mol to about 5000 g/mol or derived from a mixture of such hydrocarbylene groups. Other exemplary dispersants include succinic acid-esters and amides, alkylphenol-polyamine-coupled Mannich adducts, their capped derivatives, and other related components. Such additives may be used in an amount of 0.1 wt % to 20 wt %, such as 0.1 wt % to 8 wt %, such as 1 wt % to 6 wt % (on an as-received basis) based on the weight of the total lubricant.

Pour Point Depressants

Pour point depressants (also known as lube oil flow improvers) may also be present in lubricating oils of the present disclosure. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of from 0 wt % to about 0.5 wt %, such as about 0.0001 wt % to about 0.3 wt %, such as about 0.001 wt % to about 0.1 wt %, based on the weight of the lubricating oil.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles, thiadiazoles and mixtures thereof. Such additives may be used in an amount of about 0.01 wt % to about 5 wt %, such as about 0.01 wt % to about 1.5 wt % %, such as about 0.01 wt % to about 0.2 wt %, such as about 0.01 wt % to about 0.1 wt % based on the total weight of the lubricating oil.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of from about 0.01 wt % to about 3 wt %, such as about 0.01 wt % to about 2 wt % based on the total weight of the lubricating oil.

Anti-Foam Agents

Anti-foam agents may be included in lubricant oils of the present disclosure. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is about 1 wt % or less, such as from about 0.001 wt % to about 0.5 wt %, such as from about 0.001 wt % to about 0.2 wt %, such as from about 0.0001 wt % to about 0.15 wt %, based on the total weight of the lubricating oil.

Inhibitors and Antirust Additives

Anti-rust additives (or corrosion inhibitors) are additives that protect lubricated metal surfaces against chemical attack by water or other contaminants. One type of anti-rust additive is a polar compound that wets the metal surface, protecting the metal surface with a film of oil. Another type of anti-rust additive absorbs water by incorporating it in a water-in-oil emulsion so that only the oil touches the metal surface. Yet another type of anti-rust additive chemically adheres to the metal to produce a non-reactive surface. Examples of suitable additives include zinc dithiophosphates, metal phenolates, basic metal sulfonates, fatty acids and amines. Other anti-wear additives include zinc dithiocarbamates, molybdenum dialkyldithiophosphates, molybdenum dithiocarbamates, other organo molybdenum-nitrogen complexes, sulfurized olefins, etc. Such additives may be used in an amount of from about 0.01 wt % to about 5 wt %, such as from about 0.01 wt % to about 1.5 wt % based on the total weight of the lubricating oil.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 $cm^{-1}$ and an amide carbonyl band at 1620 $cm^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used are tri-nuclear molybdenum-sulfur compounds described in EP 1 040 115 and WO 99/31113 and the molybdenum complexes described in U.S. Pat. No. 4,978,464.

Diesel Fuels

In at least one embodiment, a diesel fuel is a $C_6$-$C_{100}$ hydrogenated polyolefin product, such as a $C_4$-$C_{25}$ hydrogenated polyolefin product.

Generally, diesel engines operate well with a cetane number of from 48 to 80, such as from 51 to 60. Fuels with a lower cetane number have longer ignition delays, requiring more time for the fuel combustion process to be completed. Hence, higher speed diesel engines operate more effectively with higher cetane number fuels. A hydrogenated polyolefin product of the present disclosure can be useful as a diesel fuel, as indicated by advantageous cetane numbers. For example, a hydrogenated polyolefin product can have a cetane number of about 30 or greater, such as about 40 or greater, such as about 45 or greater, such as about 48 or greater, such as about 50 or greater, such as about 60 or greater, such as about 70 or greater, such as about 80 or greater, such as about 90 or greater.

EXPERIMENTAL

General Methods.

All manipulations of air- and or water-sensitive compounds were carried out under dry nitrogen using a Braun UniLab drybox or standard Schlenk techniques. $^1H$ and $^{13}C$ NMR spectra of polymers were recorded on a Bruker (400 MHz) spectrometer and referenced versus residual nondeuterated solvent shifts. The product samples were dissolved in chloroform-d or toluene-$d^8$ in a 5-mm O.D. tube. Average molecular weights were determined by GC measurements. The kinematic viscosities at 40° C. and 100° C. were measured using a Stabinger viscometer. The results were then used to calculate the viscosity index.

Materials.

Toluene was purchased from Millipore and dried over fresh 4 Å molecular sieves before use. Chloroform was purchased from Aldrich and dried over 4 Å molecular sieves before use. 1-Pentene, 2-pentene, 2-methyl-2-butene, 2-methyl-1-butene, 3-methyl-1-butene (Alfa Aeser) were stirred over molecular sieves for several days and stored under nitrogen prior to use. Diethylaluminum ethoxide (AlEt$_2$OEt), MAO, and nickel-(hfacac)$_2$ were purchased from Sigma-Aldrich and used as received.

General Procedure for Olefin Oligomerization.

Oligomerization reactions were carried out in oven dried glass vials equipped with Teflon stir bars in a nitrogen atmosphere. After the desired reaction time (from 0.1 hours to 72 hours), the reactions were quenched by filtering through a non-dried silica pad, stir bars were removed, and the mixture was analyzed by GC, versus an adamantane internal standard.

Examples

Tri-substituted olefins are typically a major component in a fluid catalytic cracking (FCC) feed (see example of $C_5$-olefins distribution (%) in the FCC feed. FIG. 1). New hydrocarbon products, such as low molecular range (e.g., $C_{10}$ to $C_{25}$) polyolefin products were obtained from the conversion of di-substituted olefins (e.g., 2-methyl-1-pentene) and tri-substituted olefins (e.g., 2-methyl-2-butene) using a catalyst system of Catalyst 1 and AlEt$_2$OEt. Catalyst 1 can also be referred to as "Ni(hfacac)$_2$". Examples 1-26 were prepared using Catalyst 1 and AlEt$_2$OEt.

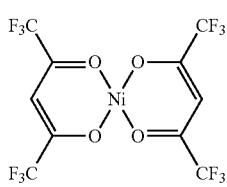

Catalyst 1

The catalyst precursors were first activated using AlEt$_2$OEt, then the general procedure for olefin polymerization was performed. The compositions and properties of isolated olefin oligomers were analyzed and compared with reference materials.

Figure 3:
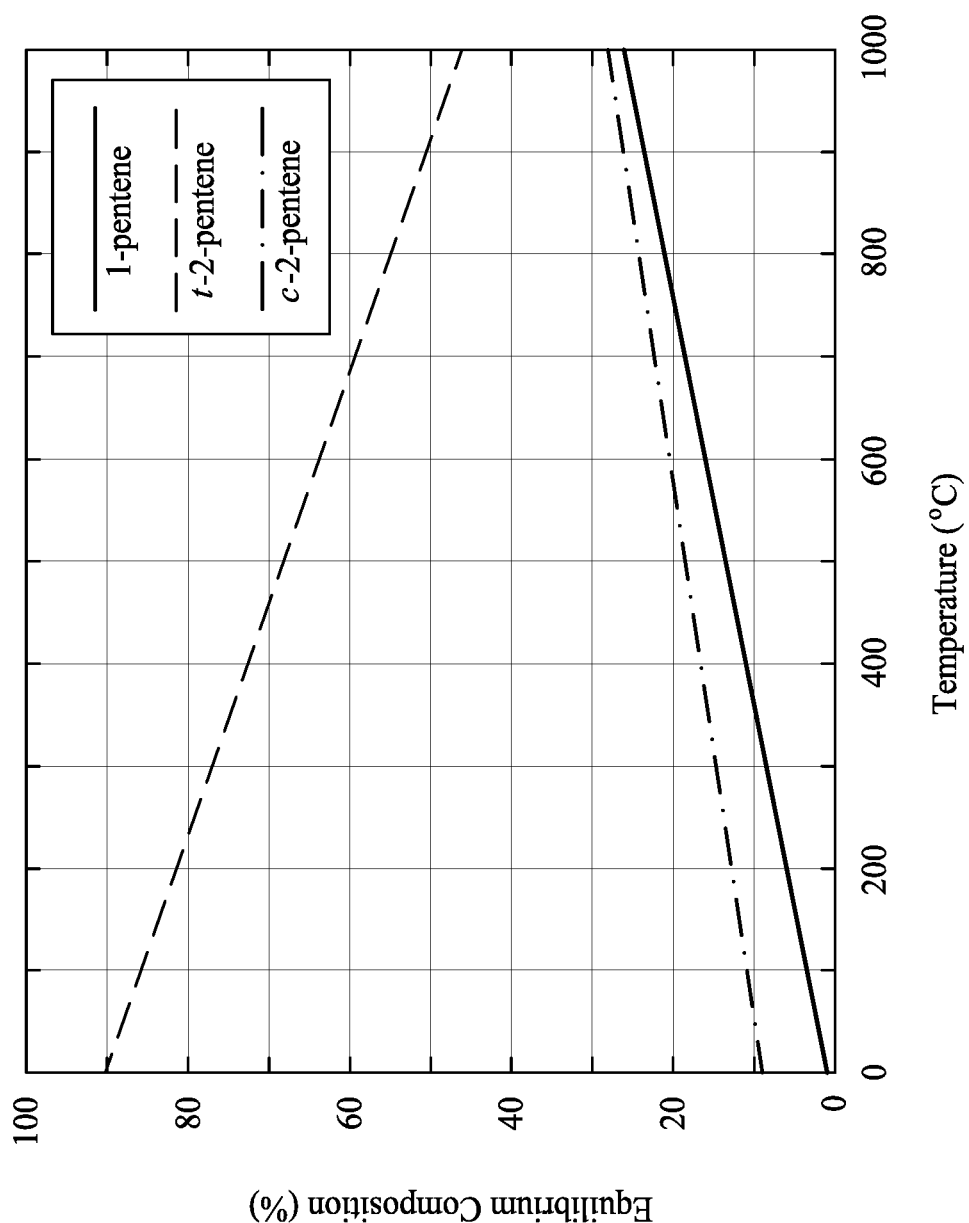
FIG. 3 is a graph illustrating equilibrium compositions (%) as a function of temperature (° C.) of 1-pentene, trans-2-pentene, and cis-2-pentene, according to one embodiment.

For example, Ni-catalyzed oligomerization of 2-methyl-2-butene led to the formation of predominantly dimers having the hydrocarbon structures of five geometric isomers represented in Scheme 1 below, with 2,6-dimethyloctane and 2,3,6-trimethylheptane being the two major polyolefin products formed.

mixture of 1-pentene, trans-2-pentene, and cis-2-pentene, as a function of temperature (° C.) is illustrated in FIG. 3. For example, at 50° C., the equilibrium compositions (%) of the thermodynamic mixture was less than 2% of 1-pentene, about 10% of cis-2-pentene, and about 88% of trans-2-pentene.

Table 2 illustrates the hydrogenated polyolefin products formed from the polyolefin products first formed by the polymerization of 1-pentene, 2-pentene, 3-Me-1-butene, 2-Me-1-butene, and 2-Me-2-butene, with Ni(hfacac)$_2$/Et$_2$AlOEt, followed by hydrogenation of the polyolefin products (mainly dimers). The polyolefin products were hydrogenated by using a Ni catalyst under 500 psig H$_2$.

Figure 4:
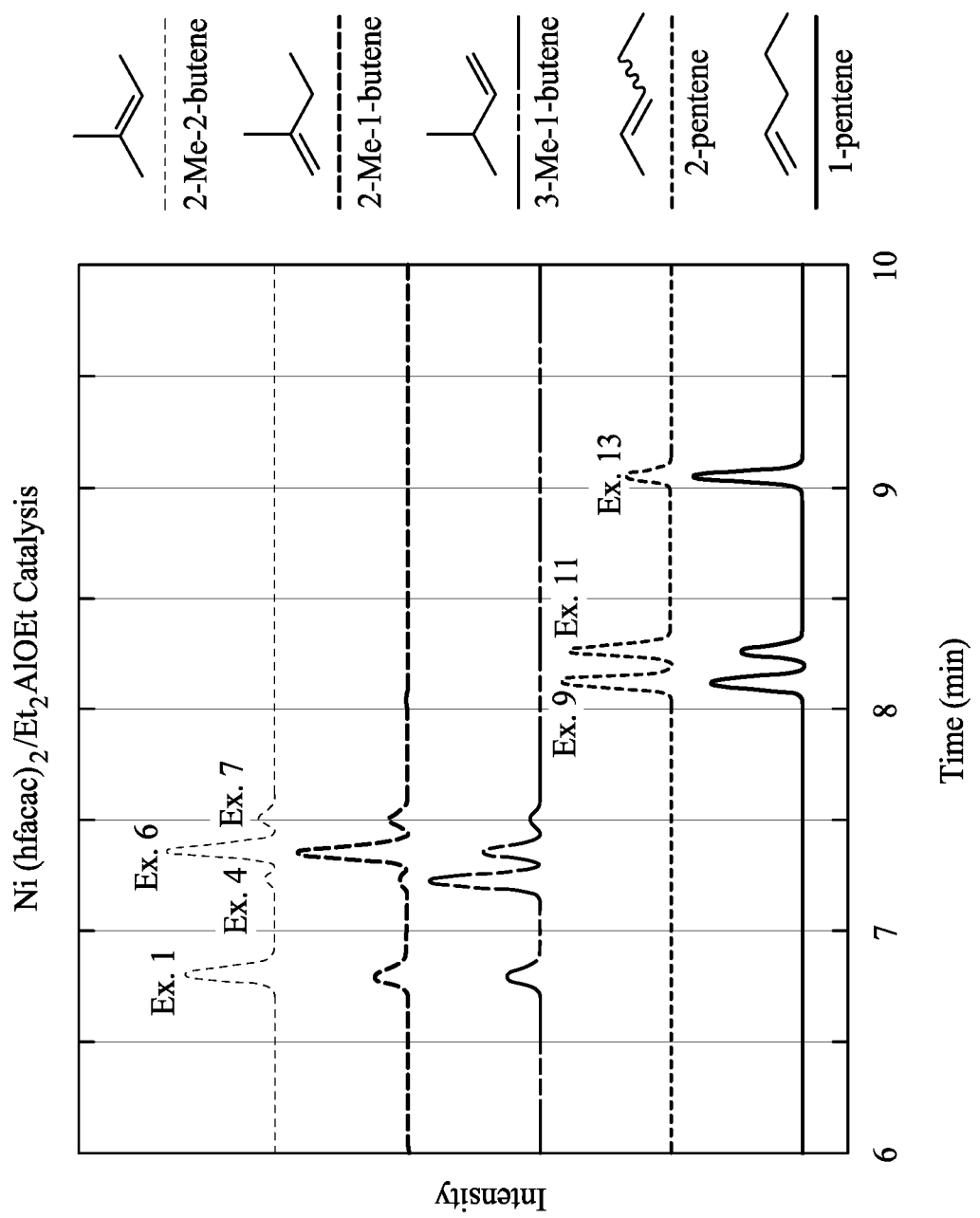
FIG. 4 is a gas chromatogram of hydrogenated polyolefin products formed from 1-pentene, 2-pentene, 3-Me-1-butene, 2-Me-1-butene, and 2-Me-2-butene with Ni(hfacac)$_2$/Et$_2$AlOEt, according to one embodiment.
Figure 4:
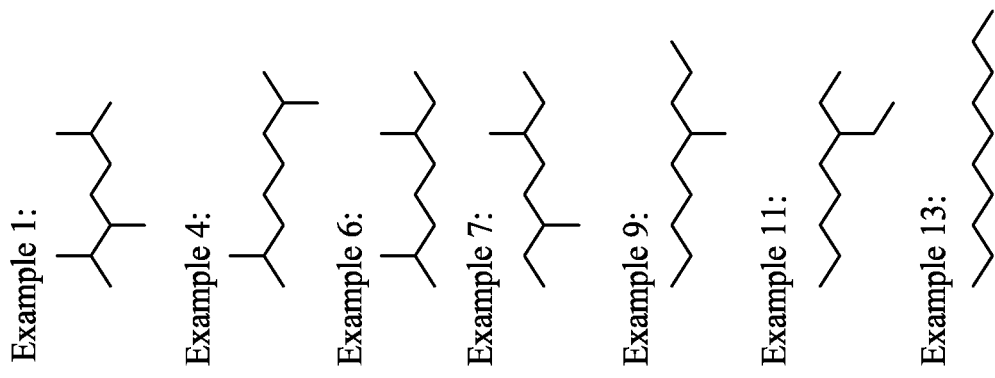

The formation of the hydrogenated polyolefin products were also observed via gas chromatography (FIG. 4), demonstrating that all C$_5$-olefins can be oligomerized. The results confirmed that 2,6-dimethyloctane and 2,3,6-trimethylheptane were the major compositions obtained via the polymerization/hydrogenation reactions when 2-Me-2-butene is used. Polymerization of 1-pentene with Ni(hfacac)$_2$/Et$_2$AlOEt, or 2-pentene with Ni(hfacac)$_2$/Et$_2$AlOEt, followed by the hydrogenation of the resulting dimers, led in both cases to the formation of three major hydrogenated polyolefin products: 4-Me-octane, 3-Et-octane, and decane.

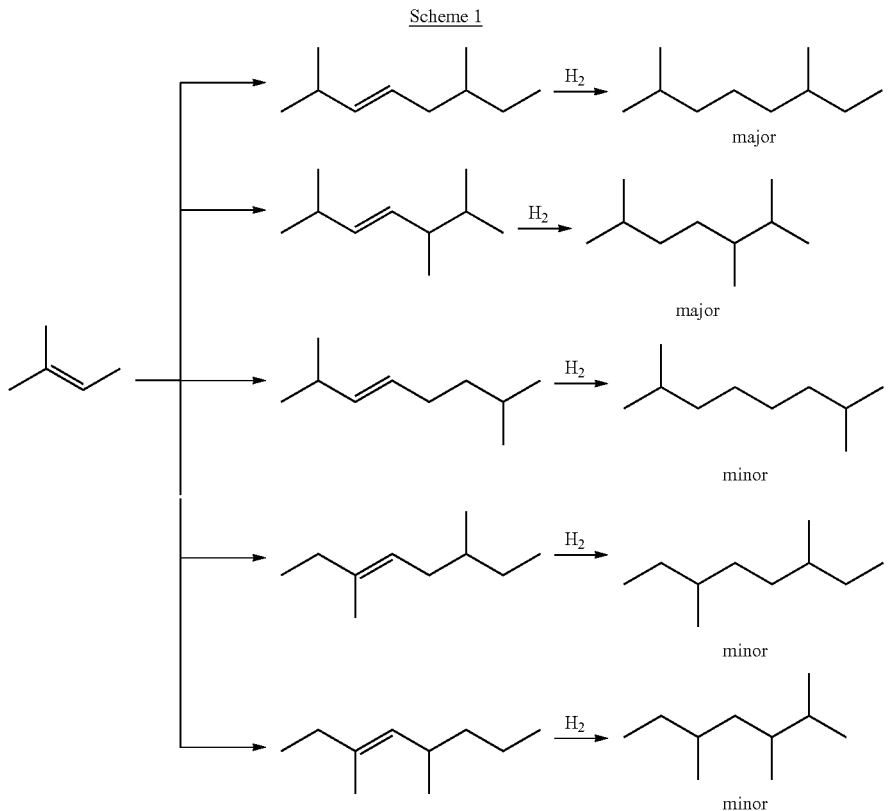

Scheme 1

Figure 2:
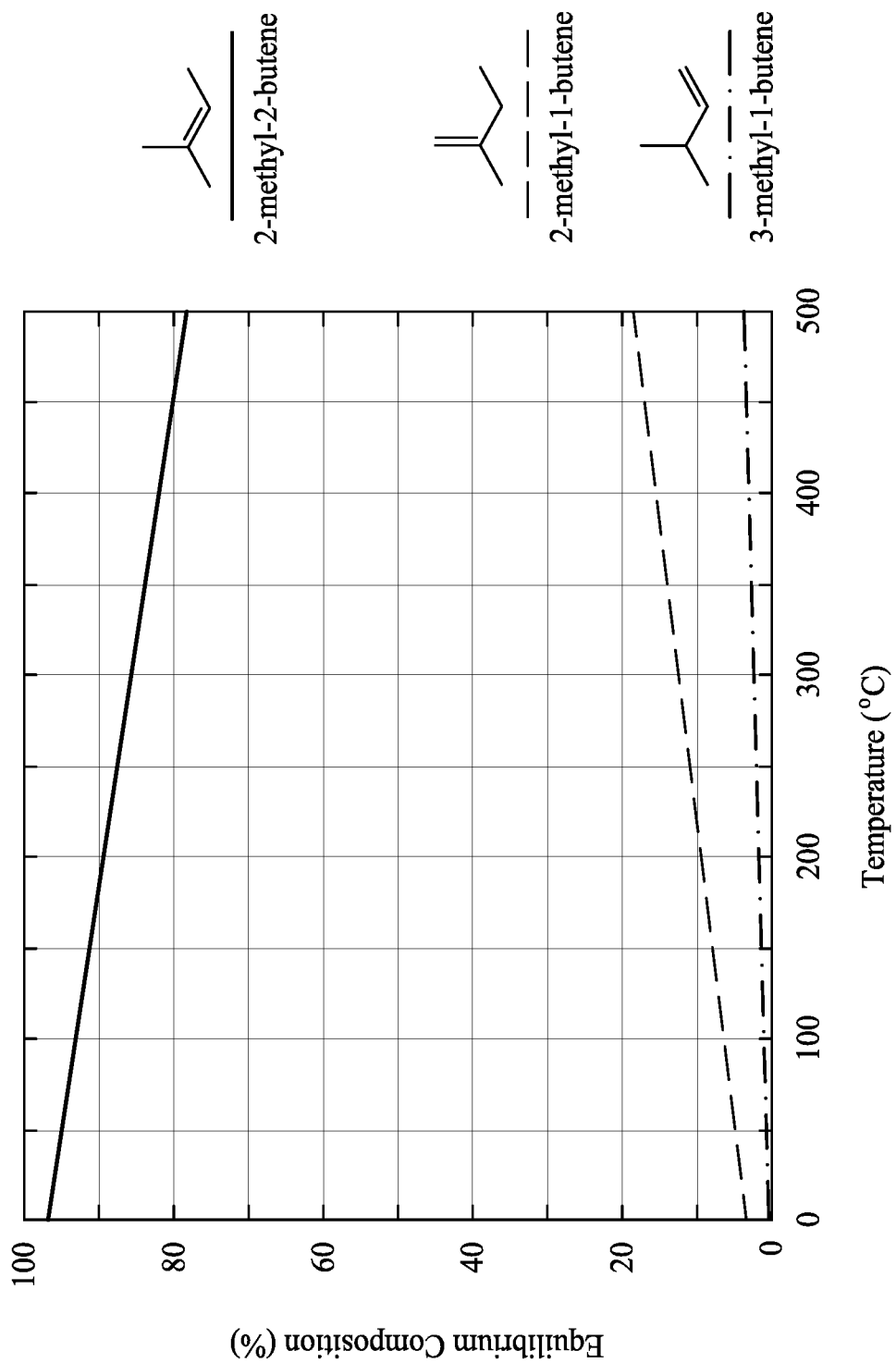
FIG. 2 is a graph illustrating equilibrium composition (%) as a function of temperature (° C.) of 2-methyl-2-butene, 2-methyl-1-butene, and 3-methyl-1-butene, according to one embodiment.

A graph illustrating the equilibrium compositions (%) (percentage of each C$_5$ branched olefins content at chemical equilibrium in an FCC reactor) of the thermodynamic mixture of 2-methyl-2-butene, 2-methyl-1-butene and 3-methyl-1-butene as a function of temperature (° C.) is illustrated in FIG. 2. At a temperature of from 0° C. to 500° C., 2-methyl-2-butene remained the major component (about 80% to 98%, based on the total C$_5$-olefins content of the thermodynamic mixture).

A graph illustrating the equilibrium compositions (%) (percentage of each C$_5$ linear olefins content at chemical equilibrium in the FCC reactor) of the thermodynamic

TABLE 2

| | | Process | | | | |
|---|---|---|---|---|---|---|
| | | 1 | 2 | 3 | 4 | 5 |
| | | | | Olefin Used | | |
| Example | Alkane | 1-pentene | 2-pentene | 2-Me-2-butene | 3-Me-1-butene | 2-Me-1-butene |
| 1 | 2,3,6-trimethyl-heptane | 0% | 0% | 38% | 16% | 20% |
| 2 | 2,3,5-trimethyl-heptane | 0% | 0% | 3% | 1% | 1% |
| 3 | 2,5-dimethyl-octane | 0% | 0% | 0% | 0% | 0% |
| 4 | 2,7-dimethyl-octane | 0% | 0% | 5% | 49% | 4% |
| 5 | 5-ethyl-2-methyl-heptane | 0% | 0% | 0% | 0% | 0% |
| 6 | 2,6-dimethyl-octane | 0% | 0% | 46% | 29% | 63% |
| 7 | 3,6-dimethyl-octane | 0% | 0% | 9% | 4% | 12% |
| 8 | 2,3-dimethyl-octane | 0% | 0% | 0% | 0% | 0% |
| 9 | 4-Me-nonane | 34% | 43% | 0% | 0% | 0% |
| 10 | 2-Me-nonane | 0% | 0% | 0% | 0% | 0% |
| 11 | 3-Et-octane | 23% | 40% | 0% | 0% | 0% |
| 12 | 3-Me-nonane | 0% | 0% | 0% | 0% | 0% |
| 13 | Decane | 38% | 16% | 0% | 0% | 0% |

Table 3 illustrates the hydrogenated polyolefin products formed from a mixed feed of 1-pentene with 2-Me-2-butene, and 2-pentene with 2-Me-2-butene, using Ni(hfacac)$_2$/Et$_2$AlOEt. Under such conditions, 4-Me-nonane, 3-Et-octane, and decane remained the major hydrogenated polyolefin products formed. New compositions were obtained as well, such as 3-Me-nonane and 2-Me-nonane, which are ideal for cetane number.

TABLE 3

| | | Process | |
|---|---|---|---|
| | | 6 | 7 |
| | | Olefin Used | |
| Example | Alkane | 1-pentene/2-Me-2-butene | 2-pentene/2-Me-2-butene |
| 14 | 2,3,6-trimethylheptane | 5% | 3% |
| 15 | 2,3,5-trimethylheptane | 0% | 0% |
| 16 | 2,5-dimethyloctane | 6% | 6% |
| 17 | 2,7-dimethyloctane | 1% | 5% |
| 18 | 5-ethyl-2-methylheptane | 5% | 4% |
| 19 | 2,6-dimethyloctane | 8% | 1% |
| 20 | 3,6-dimethyloctane | 2% | 0% |
| 21 | 2,3-dimethyloctane | 9% | 9% |
| 22 | 4-Me-nonane | 18% | 25% |
| 23 | 2-Me-nonane | 4% | 3% |
| 24 | 3-Et-octane | 12% | 23% |
| 25 | 3-Me-nonane | 12% | 12% |
| 26 | Decane | 18% | 8% |

Table 4 illustrates olefin conversion (%) and TON data of polymerizations using Ni(hfacac)$_2$/Et$_2$AlOEt and a reaction time of 1 day. Ni(hfacac)$_2$/Et$_2$AlOEt was highly active for all alpha-olefins and internal olefins. The highest Ni(hfacac)$_2$/Et$_2$AlOEt catalyst activity was found to be towards 1-pentene, with a 93% conversion (TON=163) achieved after 1 day.

TABLE 4

| Olefin | Conversion (1 day) | Turn-over Number (TON) |
|---|---|---|
| 1-pentene | 93% | 163 |
| 2-pentene | 64% | 112 |
| 3-methyl-1-butene | 33% | 58 |
| 2-methyl-1-butene | 16% | 28 |
| 2-methy-2-butene | 15% | 26 |

Figure 5:
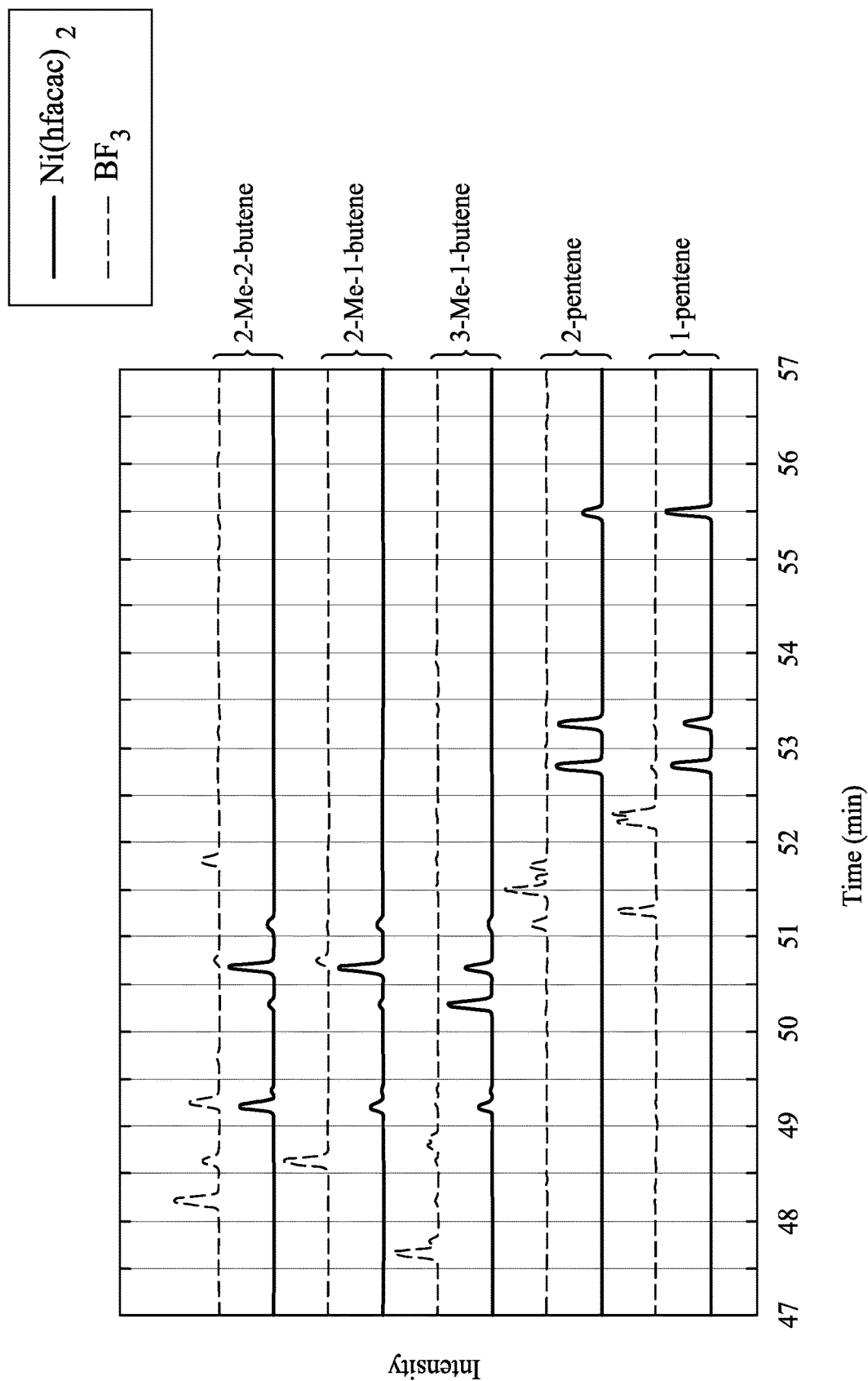
FIG. 5 is a graph illustrating gas chromatograms of dimers formed based on Ni-catalyzed C5-olefin dimerization and BF$_3$-catalyzed C5-olefin dimerization, according to one embodiment.

FIG. 5 is a graph illustrating overlaid gas chromatograms of dimers formed based on Ni(hfacac)$_2$/Et$_2$AlOEt-catalyzed C$_5$-olefin dimerization (non-acid catalysts) and BF$_3$-catalyzed C$_5$-olefin dimerization (acid catalysts). The dimers of the C$_5$-olefins (e.g., 1-pentene, 2-pentene, 3-Me-1-butene, 2-Me-1-butene, and 2-Me-2-butene) made by BF$_3$-catalyst typically showed significantly lower GC retention times than dimers of the C$_5$-olefins (e.g., 1-pentene, 2-pentene, 3-Me-1-butene, 2-Me-1-butene, and 2-Me-2-butene) made by Ni(hfacac)$_2$/Et$_2$AlOEt-catalyst, indicating that the compositions formed from BF$_3$-catalyzed polymerization have lower boiling to point and more branched isomers than that of the compositions formed from Ni(hfacac)$_2$/Et$_2$AlOEt-catalyzed polymerization. The non-acid catalysts (e.g., Ni(hfacac)$_2$/Et$_2$AlOEt) give a different, less-branched, hydrocarbon structure in the products than the acid catalysts (e.g., BF$_3$-catalyst), which can find use in diesel, lubricant or intermediates markets.

Besides functioning as base stocks, the novel compositions exhibit interesting properties for use as diesel, low sulfur products, because of one or more of the following properties: little to no aromatics, little to no paraffinic products, cold flow properties, low temperature properties, good jet fuel, better oxygen stability, good freezing point, little to no particulates.

Overall, processes of the present disclosure can provide polymerization of low molecular weight alpha-olefins, branched internal olefins, and or linear internal olefins. Polyolefin products and hydrogenated polyolefin products of the present disclosure can provide one or more of improved flow, low temperature properties, thickening efficiency, and cetane number.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A process comprising:
    introducing, neat or in the presence of a solvent, a feed comprising branched $C_5$-$C_{30}$ internal olefins comprising tri-substituted olefins to a catalyst system comprising a catalyst compound,
    wherein the catalyst compound is represented by Formula (I):

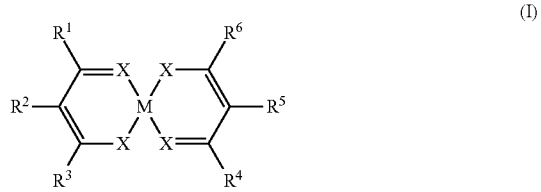

wherein:
M is a group 8, 9, 10, or 11 metal;
    each X is a heteroatom; and
    each of $R^1$, $R^3$, $R^4$, and $R^6$ is independently selected from $C_1$-$C_{40}$ hydrocarbyl, $C_1$-$C_{40}$ substituted hydrocarbyl, a heteroatom or a heteroatom-containing group, each of $R^2$ and $R^5$ is independently selected from hydrogen, $C_1$-$C_{40}$ hydrocarbyl, $C_1$-$C_{40}$ substituted hydrocarbyl, a heteroatom or a heteroatom-containing group, wherein at least one of $R^1$, $R^2$, $R^3$, $R^4$, $R^5$, and $R^6$ is a heteroatom or a heteroatom-containing group, or one or more of $R^1$ and $R^2$, $R^2$ and $R^3$, $R^4$ and $R^5$, or $R^5$ and $R^6$ are joined to form one or more substituted hydrocarbyl rings, unsubstituted hydrocarbyl rings, substituted heterocyclic rings, or unsubstituted heterocyclic rings each having 5, 6, 7, or 8 ring atoms, wherein at least one of the rings is substituted with a heteroatom or a heteroatom-containing group if the remainder of R groups of Formula (I) are not a heteroatom or a heteroatom-containing group; and obtaining a $C_6$-$C_{100}$ polyolefin product having one or more of:
    one olefin containing 2 sp$^2$ hybridized carbons,
    a methylene content of from about 1 wt % to about 98 wt %, based on the total weight of the $C_6$-$C_{100}$ polyolefin product, and
    a methyl content of from about 1 wt % to about 75 wt %, based on the total weight of the $C_6$-$C_{100}$ polyolefin product.

2. The process of claim 1, wherein the feed further comprises a linear $C_4$-$C_{30}$ internal olefin.

3. The process of claim 1, wherein the feed further comprises a $C_2$-$C_{30}$ alpha-olefin.

4. The process of claim 1, wherein the feed further comprises a linear $C_4$-$C_{30}$ internal olefin and a $C_2$-$C_{30}$ alpha-olefin.

5. The process of claim 1, wherein the heteroatom is fluorine.

6. The process of claim 1, wherein the feed further comprises one or more $C_5$ olefins selected from 2-Me-2-butene, 2-Me-1-butene, 3-Me-1-butene, 1-pentene, cis-2-pentene, trans-2-pentene, or mixture thereof.

7. The process of claim 1, wherein at least one of $R^1$, $R^2$, $R^3$, $R^4$, $R^5$, and $R^6$ are independently selected from a halogen or a halogen-containing group.

8. The process of claim 1, wherein each of $R^1$, $R^3$, $R^4$, and $R^6$ is $CF_3$ and each of $R^2$ and $R^5$ is independently selected from hydrogen, methyl, isopropyl, or fluorine.

9. The process of claim 8, wherein M is Ni.

10. The process of claim 1, wherein introducing comprises introducing the feed to the catalyst system comprising the catalyst compound and an activator.

11. The process of claim 10, wherein the catalyst system further comprises a support material.

12. The process of claim 10, wherein the activator comprises an alkylaluminoxane.

13. The process of claim 1, wherein introducing is performed in the presence of a solvent selected from n-hexane, n-heptane, cyclohexane, benzene, toluene, xylenes, or a mixture thereof.

14. The process of claim 1, wherein introducing is performed in the presence of a solvent at a ratio of an olefin to solvent of from about 1:0 to about 1:10.

15. The process of claim 1, wherein a molar ratio of catalyst to activator is from 10:1 to about 1:1,000.

16. The process of claim 15, wherein the molar ratio of catalyst to activator is about 1:3.

17. The process of claim 1, wherein a catalyst loading is from about 0.0001 mol % to about 5 mol %.

18. The process of claim 1, wherein a turnover number (TON) of the catalyst is of from about 10 to about 10,000.

19. The process of claim 1, wherein introducing is performed at a temperature of from about 20° C. to about 250° C.

20. The process of claim 19, wherein introducing is performed at a pressure of from 0 psig to about 1,000 psig.

21. The process of claim 20, wherein the reaction time is from 1 minute to 72 hours.

22. The process of any of claim 1 comprising: polymerizing the feed of claim 1 by contacting the branched $C_5$-$C_{30}$ internal olefin with the catalyst, in one or more polymerization reactors, in series or in parallel, at a reactor pressure of from 0 psig to about 1,000 psig and a reactor temperature from about 120° C. or less, to form the $C_6$-$C_{100}$ polyolefin product.

23. The process of any of claim 1 comprising: polymerizing the feed of claim 2 comprising a linear $C_4$-$C_{30}$ internal olefin by contacting the linear $C_4$-$C_{30}$ internal olefin with the catalyst, in one or more polymerization reactors, in series or in parallel, at a reactor pressure of from 0 psig to about 1,000 psig, and a reactor temperature from about 120° C. or less, to form the $C_6$-$C_{100}$ polyolefin product.

24. The process of claim 1, wherein the feed is converted to the $C_6$-$C_{100}$ polyolefin product at a conversion (%) of from about 2% to about 99%.

* * * * *